United States Patent
Cowsert et al.

(10) Patent No.: US 6,602,857 B1
(45) Date of Patent: Aug. 5, 2003

(54) ANTISENSE MODULATION OF PTP1B EXPRESSION

(76) Inventors: Lex M. Cowsert, 3008 Newshire St., Carlsbad, CA (US) 92008; Jacqueline Wyatt, 1065 Hymettus Ave., Encinitas, CA (US) 92024; Brett P. Monia, 7605 Nueva Castilla Way, La Costa, CA (US) 96056; Madeline M. Butler, 15951 Avenida Calma, Rancho Santa Fe, CA (US) 92091; Robert McKay, 277 Caminito Pescado #73, San Diego, CA (US) 92107

( * ) Notice: Subject to any disclaimer, the term of this patent is extended or adjusted under 35 U.S.C. 154(b) by 0 days.

(21) Appl. No.: 09/629,644

(22) Filed: Jul. 31, 2000

Related U.S. Application Data

(63) Continuation-in-part of application No. 09/487,368, filed on Jan. 18, 2000.

(51) Int. Cl.$^7$ .......................... A61K 38/28; C12Q 1/68; C12P 19/34; C12N 15/63; C07H 21/02
(52) U.S. Cl. .......................... 514/44; 435/6; 435/91.1; 435/375; 435/455; 536/23.1; 536/24.5; 536/25.3
(58) Field of Search .......................... 435/6, 91.1, 375; 536/23.1, 24.5; 514/44

(56) References Cited

U.S. PATENT DOCUMENTS

| | | | | |
|---|---|---|---|---|
| 5,726,027 A | * | 3/1998 | Olefsky | ...................... 435/7.21 |
| 5,801,154 A | * | 9/1998 | Baracchini et al. | ............ 514/44 |
| 6,261,840 B1 | | 7/2001 | Cowsert et al. | |

FOREIGN PATENT DOCUMENTS

| | | |
|---|---|---|
| WO | WO 97/32595 | 9/1997 |
| WO | WO01/53528 | 7/2001 |

OTHER PUBLICATIONS

Giorgio Palu' et al., In pursuit of new developments for gene therapy of human disease, Journal of Biotechnology 68 (1999) pp. 1–13.*
Stanley T. Crooke, Antisense Research and Application, pp. 1–50.*
Karen Pihl–Carey, Isis To Restructure As Crohn's Diseases Drug Fails In Phase III, the Daily Biotechnology Newspaper, vol. 10, No. 239, pp. 1–12.*
Andrea D. Branch, A good antisense molecule is hard to find, TIBS 23—Feb. 1998, pp. 45–50.*
Natalie Milner et al., Selecting effective antisense reagents on combinatiorial oligonucleotide arrays, Nature Biotechnology, vol. 15, Jun. 1997, pp. 537–541.*
Aviv Hassid et al., Antisense oligonucleotides against protein tyrosine phosphatase 1B increase focal adhesion protein phosphorylation and migration in rat aortic smooth muscle cells, Supplement I, section 1733.*

S. Huang et al., Antisense to protein tyrosine phosphatase 1B increases tyrosine phosphorylation of focal adhesion protein in aortic smooth muscle cells of rats, Vascular Cell and Molecular Biology, section 1099.*
Jonathan Chernoff et al., Cloning of a cDNA for a major human potein–tyrosine–phosphatase, Proc. Natl. Acad. Sci. USA vol. 87, pp. 2735–2739.*
M. Elchebly et al, "Increased Insulin Sensitivity and Obesity Resistance in Mice Lacking the protein Tyrosine Phosphatase–1B Gene", Science, 283:1544–1548 (Mar. 5, 1999).
D. Ferber, "Cell Biology: New Clues Found to Diabetes and Obesity", Science, 283(5407):1423–1425 (Mar. 5, 1999).
Arregui et al., Impaired integrin–mediated adhesion and signaling in fibroblasts expressing a dominant–negative mutant PTP1B, J. Cell. Biol., 1998, 143:861–873.
Balsamo et al., The nonreceptor protein tyrosine phosphatase PTP1B binds to the cytoplasmic domain of N–cadherin and regulates the cadherin–actin linkage, J. Cell. Biol., 1998, 143:523–532.
Brown–Shimer et al., Effect of protein tyrosine phosphatase 1B expression on transformation by the human neu oncogene, Cancer Res., 1992, 52:478–482.
Chen et al., A phosphotyrosyl mimetic peptide reverses impairment of insulin– stimulated translocation of GLUT4 caused by overexpression of PTP1B in rat adipose cells, Biochemistry, 1999, 38:384–389.
Chen et al., Protein–tyrosine phosphatases PTP1B and syp are modulators of insulin– stimulated translocation of GLUT4 in transfected rat adipose cells, J. Biol. Chem., 1997, 272:8026–8031.
Desmarais et al., Inhibition of protein tyrosine phosphatases PTP1B and CD45 by sulfotyrosyl peptides, Arch. Biochem. Biophys., 1998, 354:225–231.
Elcheby et al., Increased insulin sensitivity and obesity resistance in mice lacking the protein tyrosine phosphatase–1B gene [see comments], Science, 1999, 283:1544–1548.
Goldstein et al., Regulation of the insulin signalling pathway by cellular protein– tyrosine phosphatases, Mol. Cell, Biochem., 1998, 182:91–99.
Ham et al, Selective inactivation of protein tyrosine phosphatase PTP1B by Sulfone analogue of naphthoquinone [In Process Citation], Bioorg. Med. Chem. Lett., 1999, 9:185–186.
LaMontagne et al., Protein tyrosine phosphatase PTP1B suppresses p210 bcr–abl–induced transformation of rat–1 fibroblasts and promotes differentiation of K562 cells, Proc. Natl. Acad. Sci. U. S. A., 1998, 95:14094–14099.

(List continued on next page.)

Primary Examiner—Ram R. Shukla

(57) ABSTRACT

Compounds, compositions and methods are provided for modulating the expression of PTP1B. The compositions comprise antisense compounds, particularly antisense oligonucleotides, targeted to nucleic acids encoding PTP1B. Methods of using these compounds for modulation of PTP1B expression and for treatment of diseases associated with expression of PTP1B are provided.

72 Claims, No Drawings

OTHER PUBLICATIONS

Lee et al., Reversible inactivation of protein–tyrosine phosphatase 1B in A431 cells stimulated with epidermal growth factor, *J. Biol. Chem.*, 1998, 273:15366–15372.

Liu et al., Protein tyrosine phosphatase 1B interacts with and is tyrosine phosphorylated by the epidermal growth factor receptor, *Biochem. J.*, 1997, 327:139–145.

Liu et al., Protein tyrosine phosphatase 1B negatively regulates integrin signaling, *Curr. Biol.*, 1998, 8:173–176.

Liu et al., Transformation suppression by protein tyrosine phosphatase 1B requires a functional SH3 ligand, *Mol. Cell. Biol.*, 1998, 18:250–259.

Roller et al., Potent inhibition of protein–tyrosine phosphatase–1B using the phosphotyrosyl mimetic fluoro–O–malonyl tyrosine (FOMT), *Bioorg. Med. Chem. Lett.*, 1998, 8:2149–2150.

Schievella et al., Protein tyrosine phosphatase 1B undergoes mitosis–specific phosphorylation on serine, *Cell. Growth Differ.*, 1993, 4:239–246.

Seely et al., Protein tyrosine phosphatase 1B interacts with the activated insulin receptor, *Diabetes*, 1996, 45:1379–1385.

Sell et al., Insulin–inducible changes in the relative ratio of PTP1B splice variants, *Mol. Genet. Metab.*, 1999, 66:189–192.

Shifrin et al., Growth factor–inducible alternative splicing of nontransmembrane phosphotyrosine phosphatase PTP–1B pre–mRNA, *J. Biol. Chem.*, 1993, 268:25376–25384.

Skorey et al., How does alendronate inhibit protein–tyrosine phosphatases?, *J. Biol. Chem.*, 1997, 272:22472–22480.

Taing et al., Potent and highly selective inhibitors of the protein tyrosine phosphatase 1B, *Biochemistry*, 1999, 38:3793–3803.

Taylor et al., Potent non–peptidyl inhibitors of protein tyrosine phosphatase 1B [published erratum appears in Bioorg Med Chem 1998 Nov.; 6(11) :2235], *Bioorg. Med. Chem.*, 1998, 6:1457–1468.

Tonks et al., Characterization of the major protein–tyrosine–phosphatases of human placenta, *J. Biol. Chem.*, 1988, 263:6731–6737.

Tonks et al., Purification of the major protein–tyrosinephosphatases of human placenta, *J. Biol. Chem.*, 1988, 263:6722–6730.

Wang et al., Naphthalenebis[alpha, alpha–difluoromethylenephosphonates] as potent inhibitors of protein tyrosine phosphatases, *Bioorg. Med. Chem. Lett.*, 1998, 8:345–350.

Wang et al., Mechanism of inhibition of protein–tyrosine phosphatases by disodium aurothiomalate, *Biochem. Pharmacol.*, 1997, 54:703–711.

Wiener et al., Overexpression of the tyrosine phosphatase PTP1B is associated with human ovarian carcinomas, *Am. J. Obstet. Gynecol.*, 1994, 170:1177–1183.

Yao et al., Structure–based design and synthesis of small molecule protein–tyrosine phosphatase 1B inhibitors, *Bioorg. Med. Chem.*, 1998, 6:1799–1810.

Zhang, Protein–tyrosine phosphatases: biological function, structural characteristics, and mechanism of catalysis, Crit. Rev. Biochem. *Mol. Biol.*, 1998, 33:1–52.

R. Crystal, "Transfer of Genes to Humans: Early Lessons and Obstacles to Success", *Science*, 270:404–410 (1995).

T. Friedmann, "Overcoming the Obstacles –Treating Disease by Providing Needed Genes Remains a Compelling Idea, But Clinical and Basic Researchers Still Have Much to do Before Gene Therapy Can Live Up to its Promise", *Scientific American*, pp. 96–101 (Jun. 1997).

W. James, Towards Gene–Inhibition Therapy: A Review of Progress and Prospects in the Field of Antiviral Antisense Nucleic Acids and Ribozymes:, *Antiviral Chemistry & Chemotherapy*, 2(4): 191–214 (1991).

J. Schofield et al., "Non–Viral Approaches to Gene Therapy", *British Medical Bulletin*, 51(1): 56–71 (1995).

I. Verma et al., "Gene Therapy –Promises, Problems and Propects", *Nature*, 389:239–242 (Sep. 18, 1997).

Graham et al., "In Vivo Distribution and Metabolism of a Phosphorothioate Oligonucleotide within Rat Liver after Intravenous Administration" The Journal of Pharmacology and Experimental Therapeutics, vol, 286, No. 1, 447–458 (1998).

Hassid et al., "NO Alters Cell Shape and Motility in Aortic Smooth Muscle Cells via Protein Tyrosine Phosphatase 1B Activation", Am. J. Phys. 277(3) part 2:H1014–1026 (Sep. 1999).

Hassid et al., "Role of PTP–1B in Aortic Smooth Muscle Cell Motility and Tyrosine Phosphorylation of Focal Adhesion Proteins", Am. J. Phys. 277(1)part 2:H192–198 (Jul. 1999).

Guan et al. "Cloning and Expression of Protein–Tyrosine-Phosphatase", Proc. Natl. Acad. Sci. USA 87:1501–1505 (Feb. 1990).

* cited by examiner

SEQUENCE LISTING

<160> NUMBER OF SEQ ID NOS: 242

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                          20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                          20

<210> SEQ ID NO 3
<211> LENGTH: 3247
<212> TYPE: DNA
<213> ORGANISM: Homo sapiens
<220> FEATURE:
<221> NAME/KEY: CDS
<222> LOCATION: (91)...(1398)

<400> SEQUENCE: 3
gggcgggcct cggggctaag agcgcgacgc ctagagcggc agacggcgca gtgggccgag      60
aaggaggcgc agcagccgcc ctggcccgtc atg gag atg gaa aag gag ttc gag     114
                                    Met Glu Met Glu Lys Glu Phe Glu
                                      1               5 cag atc gac aag tcc ggg agc tgg gcg gcc att tac cag gat atc cga      162
Gln Ile Asp Lys Ser Gly Ser Trp Ala Ala Ile Tyr Gln Asp Ile Arg
         10                  15                  20 cat gaa gcc agt gac ttc cca tgt aga gtg gcc aag ctt cct aag aac      210
His Glu Ala Ser Asp Phe Pro Cys Arg Val Ala Lys Leu Pro Lys Asn
 25                  30                  35                  40 aaa aac cga aat agg tac aga gac gtc agt ccc ttt gac cat agt cgg      258
Lys Asn Arg Asn Arg Tyr Arg Asp Val Ser Pro Phe Asp His Ser Arg
                 45                  50                  55 att aaa cta cat caa gaa gat aat gac tat atc aac gct agt ttg ata      306
Ile Lys Leu His Gln Glu Asp Asn Asp Tyr Ile Asn Ala Ser Leu Ile
             60                  65                  70 aaa atg gaa gaa gcc caa agg agt tac att ctt acc cag ggc cct ttg      354
Lys Met Glu Glu Ala Gln Arg Ser Tyr Ile Leu Thr Gln Gly Pro Leu
         75                  80                  85 cct aac aca tgc ggt cac ttt tgg gag atg gtg tgg gag cag aaa agc      402
Pro Asn Thr Cys Gly His Phe Trp Glu Met Val Trp Glu Gln Lys Ser
     90                  95                 100 agg ggt gtc gtc atg ctc aac aga gtg atg gag aaa ggt tcg tta aaa      450
Arg Gly Val Val Met Leu Asn Arg Val Met Glu Lys Gly Ser Leu Lys
105                 110                 115                 120 tgc gca caa tac tgg cca caa aaa gaa gaa aaa gag atg atc ttt gaa      498
Cys Ala Gln Tyr Trp Pro Gln Lys Glu Glu Lys Glu Met Ile Phe Glu
                125                 130                 135 gac aca aat ttg aaa tta aca ttg atc tct gaa gat atc aag tca tat      546
Asp Thr Asn Leu Lys Leu Thr Leu Ile Ser Glu Asp Ile Lys Ser Tyr -continued

|  |  |  |  |  |  |  |  |  |  |  |  |  |  |  |  |
|---|---|---|---|---|---|---|---|---|---|---|---|---|---|---|---|
|  |  | 140 |  |  |  | 145 |  |  |  | 150 |  |  |  |  |  |

```
tat aca gtg cga cag cta gaa ttg gaa aac ctt aca acc caa gaa act      594
Tyr Thr Val Arg Gln Leu Glu Leu Glu Asn Leu Thr Thr Gln Glu Thr
        155                 160                 165 cga gag atc tta cat ttc cac tat acc aca tgg cct gac ttt gga gtc      642
Arg Glu Ile Leu His Phe His Tyr Thr Thr Trp Pro Asp Phe Gly Val
    170                 175                 180 cct gaa tca cca gcc tca ttc ttg aac ttt ctt ttc aaa gtc cga gag      690
Pro Glu Ser Pro Ala Ser Phe Leu Asn Phe Leu Phe Lys Val Arg Glu
185                 190                 195                 200 tca ggg tca ctc agc ccg gag cac ggg ccc gtt gtg gtg cac tgc agt      738
Ser Gly Ser Leu Ser Pro Glu His Gly Pro Val Val Val His Cys Ser
                205                 210                 215 gca ggc atc ggc agg tct gga acc ttc tgt ctg gct gat acc tgc ctc      786
Ala Gly Ile Gly Arg Ser Gly Thr Phe Cys Leu Ala Asp Thr Cys Leu
            220                 225                 230 ctg ctg atg gac aag agg aaa gac cct tct tcc gtt gat atc aag aaa      834
Leu Leu Met Asp Lys Arg Lys Asp Pro Ser Ser Val Asp Ile Lys Lys
        235                 240                 245 gtg ctg tta gaa atg agg aag ttt cgg atg ggg ttg atc cag aca gcc      882
Val Leu Leu Glu Met Arg Lys Phe Arg Met Gly Leu Ile Gln Thr Ala
    250                 255                 260 gac cag ctg cgc ttc tcc tac ctg gct gtg atc gaa ggt gcc aaa ttc      930
Asp Gln Leu Arg Phe Ser Tyr Leu Ala Val Ile Glu Gly Ala Lys Phe
265                 270                 275                 280 atc atg ggg gac tct tcc gtg cag gat cag tgg aag gag ctt tcc cac      978
Ile Met Gly Asp Ser Ser Val Gln Asp Gln Trp Lys Glu Leu Ser His
                285                 290                 295 gag gac ctg gag ccc cca ccc gag cat atc ccc cca cct ccc cgg cca     1026
Glu Asp Leu Glu Pro Pro Pro Glu His Ile Pro Pro Pro Pro Arg Pro
            300                 305                 310 ccc aaa cga atc ctg gag cca cac aat ggg aaa tgc agg gag ttc ttc     1074
Pro Lys Arg Ile Leu Glu Pro His Asn Gly Lys Cys Arg Glu Phe Phe
        315                 320                 325 cca aat cac cag tgg gtg aag gaa gag acc cag gag gat aaa gac tgc     1122
Pro Asn His Gln Trp Val Lys Glu Glu Thr Gln Glu Asp Lys Asp Cys
    330                 335                 340 ccc atc aag gaa gaa aaa gga agc ccc tta aat gcc gca ccc tac ggc     1170
Pro Ile Lys Glu Glu Lys Gly Ser Pro Leu Asn Ala Ala Pro Tyr Gly
345                 350                 355                 360 atc gaa agc atg agt caa gac act gaa gtt aga agt cgg gtc gtg ggg     1218
Ile Glu Ser Met Ser Gln Asp Thr Glu Val Arg Ser Arg Val Val Gly
                365                 370                 375 gga agt ctt cga ggt gcc cag gct gcc tcc cca gcc aaa ggg gag ccg     1266
Gly Ser Leu Arg Gly Ala Gln Ala Ala Ser Pro Ala Lys Gly Glu Pro
            380                 385                 390 tca ctg ccc gag aag gac gag gac cat gca ctg agt tac tgg aag ccc     1314
Ser Leu Pro Glu Lys Asp Glu Asp His Ala Leu Ser Tyr Trp Lys Pro
        395                 400                 405 ttc ctg gtc aac atg tgc gtg gct acg gtc ctc acg gcc ggc gct tac     1362
Phe Leu Val Asn Met Cys Val Ala Thr Val Leu Thr Ala Gly Ala Tyr
    410                 415                 420 ctc tgc tac agg ttc ctg ttc aac agc aac aca tag cctgaccctc          1408
Leu Cys Tyr Arg Phe Leu Phe Asn Ser Asn Thr
425                 430                 435 ctccactcca cctccaccca ctgtccgcct ctgcccgcag agcccacgcc cgactagcag   1468
gcatgccgcg gtaggtaagg gccgccggac cgcgtagaga gccgggcccc ggacggacgt   1528
tggttctgca ctaaaaccca tcttccccgg atgtgtgtct caccccctcat ccttttactt  1588
```

```
tttgcccctt ccactttgag taccaaatcc acaagccatt ttttgaggag agtgaaagag    1648
agtaccatgc tggcggcgca gagggaaggg gcctacaccc gtcttgggge tcgccccacc    1708 cagggctccc tcctggagca tcccaggcgg cgcacgccaa cagccccccc cttgaatctg    1768
cagggagcaa ctctccactc catatttatt taaacaattt ttttccccaaa ggcatcccata  1828 gtgcactagc attttcttga accaataatg tattaaaatt ttttgatgtc agccttgcat    1888
caagggcttt atcaaaaagt acaataataa atcctcaggt agtactggga atggaaggct    1948
ttgccatggg cctgctgcgt cagaccagta ctgggaagga ggacggttgt aagcagttgt    2008
tatttagtga tattgtgggt aacgtgagaa gatagaacaa tgctataata tataatgaac    2068
acgtgggtat ttaataagaa acatgatgtg agattacttt gtcccgctta ttctcctccc    2128
tgttatctgc tagatctagt tctcaatcac tgctcccccg tgtgtattag aatgcatgta    2188
aggtcttctt gtgtcctgat gaaaaatatg tgcttgaaat gagaaacttt gatctctgct    2248
tactaatgtg ccccatgtcc aagtccaacc tgcctgtgca tgacctgatc attacatggc    2308
tgtggttcct aagcctgttg ctgaagtcat tgtcgctcag caatagggtg cagttttcca    2368
ggaataggca tttgctaatt cctggcatga cactctagtg acttcctggt gaggcccagc    2428
ctgtcctggt acagcagggt cttgctgtaa ctcagacatt ccaagggtat gggaagccat    2488
attcacacct cacgctctgg acatgattta gggaagcagg acaccccccc gccccccacc    2548
tttgggatca gcctccgcca ttccaagtca acactcttct tgagcagacc gtgatttgga    2608
agagaggcac ctgctggaaa ccacacttct tgaaacagcc tgggtgacgg tcctttaggc    2668
agcctgccgc cgtctctgtc ccggttcacc ttgccgagag aggcgcgtct gccccaccct    2728
caaaccctgt ggggcctgat ggtgctcacg actcttcctg caaagggaac tgaagacctc    2788
cacattaagt ggcttttta catgaaaaac acggcagctg tagctcccga gctactctct    2848
tgccagcatt ttcacatttt gcctttctcg tggtagaagc cagtacagag aaattctgtg    2908
gtgggaacat tcgaggtgtc accctgcaga gctatggtga ggtgtggata aggcttaggt    2968
gccaggctgt aagcattctg agctggcttg ttgtttttaa gtcctgtata tgtatgtagt    3028
agtttgggtg tgtatatata gtagcatttc aaaatggacg tactggttta acctcctatc    3088
cttggagagc agctggctct ccaccttgtt acacattatg ttagagaggt agcgagctgc    3148
tctgctatat gccttaagcc aatatttact catcaggtca ttatttttta caatggccat    3208
ggaataaacc attttacaa aaataaaaac aaaaaaagc                            3247

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
ggagttcgag cagatcgaca a                                              21

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
```

```
ggccactcta catgggaagt c                                              21

<210> SEQ ID NO 6
<211> LENGTH: 24
<212> TYPE: DNA
<213> ORGANISM: Artificial Sequence
<220> FEATURE:
<223> OTHER INFORMATION: PCR Probe

<400> SEQUENCE: 6
agctgggcgg ccatttacca ggat                                           24

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                 19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                20

<210> SEQ ID NO 10
<211> LENGTH: 4127
<212> TYPE: DNA
<213> ORGANISM: Rattus norvegicus
<220> FEATURE:
<221> NAME/KEY: CDS
<222> LOCATION: (120)...(1418)

<400> SEQUENCE: 10
agccgctgct ggggaggttg gggctgaggt ggtggcgggc gacgggcctc gagacgcgga    60
gcgacgcggc ctagcgcggc ggacggccga gggaactcgg gcagtcgtcc cgtcccgcc   119 atg gaa atg gag aag gaa ttc gag cag atc gat aag gct ggg aac tgg   167
Met Glu Met Glu Lys Glu Phe Glu Gln Ile Asp Lys Ala Gly Asn Trp
 1               5                  10                  15 gcg gct att tac cag gat att cga cat gaa gcc agt gac ttc cca tgc   215
Ala Ala Ile Tyr Gln Asp Ile Arg His Glu Ala Ser Asp Phe Pro Cys
             20                  25                  30 aga ata gcg aaa ctt cct aag aac aaa aac cgg aac agg tac cga gat   263
Arg Ile Ala Lys Leu Pro Lys Asn Lys Asn Arg Asn Arg Tyr Arg Asp
         35                  40                  45 gtc agc cct ttt gac cac agt cgg att aaa ttg cat cag gaa gat aat   311
Val Ser Pro Phe Asp His Ser Arg Ile Lys Leu His Gln Glu Asp Asn
     50                  55                  60
```

-continued

| | | | | | | | | | | | | | | | | |
|---|---|---|---|---|---|---|---|---|---|---|---|---|---|---|---|---|
| | 50 | | | | | 55 | | | | | 60 | | | | | |
| gac | tat | atc | aat | gcc | agc | ttg | ata | aaa | atg | gag | gaa | gcc | cag | agg | agc | 359 |
| Asp | Tyr | Ile | Asn | Ala | Ser | Leu | Ile | Lys | Met | Glu | Glu | Ala | Gln | Arg | Ser | |
| 65 | | | | 70 | | | | | 75 | | | | | 80 | | |
| tat | atc | ctc | acc | cag | ggc | cct | tta | cca | aac | acg | tgc | ggg | cac | ttc | tgg | 407 |
| Tyr | Ile | Leu | Thr | Gln | Gly | Pro | Leu | Pro | Asn | Thr | Cys | Gly | His | Phe | Trp | |
| | | | | 85 | | | | | 90 | | | | | 95 | | |
| gag | atg | gtg | tgg | gag | cag | aag | agc | agg | ggc | gtg | gtc | atg | ctc | aac | cgc | 455 |
| Glu | Met | Val | Trp | Glu | Gln | Lys | Ser | Arg | Gly | Val | Val | Met | Leu | Asn | Arg | |
| | | | 100 | | | | | 105 | | | | | 110 | | | |
| atc | atg | gag | aaa | ggc | tcg | tta | aaa | tgt | gcc | cag | tat | tgg | cca | cag | aaa | 503 |
| Ile | Met | Glu | Lys | Gly | Ser | Leu | Lys | Cys | Ala | Gln | Tyr | Trp | Pro | Gln | Lys | |
| | | 115 | | | | | 120 | | | | | 125 | | | | |
| gaa | gaa | aaa | gag | atg | gtc | ttc | gat | gac | acc | aat | ttg | aag | ctg | aca | ctg | 551 |
| Glu | Glu | Lys | Glu | Met | Val | Phe | Asp | Asp | Thr | Asn | Leu | Lys | Leu | Thr | Leu | |
| | 130 | | | | | 135 | | | | | 140 | | | | | |
| atc | tct | gaa | gat | gtc | aag | tca | tat | tac | aca | gta | cgg | cag | ttg | gag | ttg | 599 |
| Ile | Ser | Glu | Asp | Val | Lys | Ser | Tyr | Tyr | Thr | Val | Arg | Gln | Leu | Glu | Leu | |
| 145 | | | | | 150 | | | | | 155 | | | | | 160 | |
| gag | aac | ctg | gct | acc | cag | gag | gct | cga | gag | atc | ctg | cat | ttc | cac | tac | 647 |
| Glu | Asn | Leu | Ala | Thr | Gln | Glu | Ala | Arg | Glu | Ile | Leu | His | Phe | His | Tyr | |
| | | | | 165 | | | | | 170 | | | | | 175 | | |
| acc | acc | tgg | cct | gac | ttt | gga | gtc | cct | gag | tca | cct | gcc | tct | ttc | ctc | 695 |
| Thr | Thr | Trp | Pro | Asp | Phe | Gly | Val | Pro | Glu | Ser | Pro | Ala | Ser | Phe | Leu | |
| | | | 180 | | | | | 185 | | | | | 190 | | | |
| aat | ttc | cta | ttc | aaa | gtc | cga | gag | tca | ggc | tca | ctc | agc | cca | gag | cac | 743 |
| Asn | Phe | Leu | Phe | Lys | Val | Arg | Glu | Ser | Gly | Ser | Leu | Ser | Pro | Glu | His | |
| | | 195 | | | | | 200 | | | | | 205 | | | | |
| ggc | ccc | att | gtg | gtc | cac | tgc | agt | gct | ggc | att | ggc | agg | tca | ggg | acc | 791 |
| Gly | Pro | Ile | Val | Val | His | Cys | Ser | Ala | Gly | Ile | Gly | Arg | Ser | Gly | Thr | |
| | 210 | | | | | 215 | | | | | 220 | | | | | |
| ttc | tgc | ctg | gct | gac | acc | tgc | ctc | tta | ctg | atg | gac | aag | agg | aaa | gac | 839 |
| Phe | Cys | Leu | Ala | Asp | Thr | Cys | Leu | Leu | Leu | Met | Asp | Lys | Arg | Lys | Asp | |
| 225 | | | | | 230 | | | | | 235 | | | | | 240 | |
| ccg | tcc | tct | gtg | gac | atc | aag | aaa | gtg | ctg | ttg | gag | atg | cgc | agg | ttc | 887 |
| Pro | Ser | Ser | Val | Asp | Ile | Lys | Lys | Val | Leu | Leu | Glu | Met | Arg | Arg | Phe | |
| | | | | 245 | | | | | 250 | | | | | 255 | | |
| cgc | atg | ggg | ctc | atc | cag | acg | gcc | gac | caa | ctg | cgc | ttc | tcc | tac | ctg | 935 |
| Arg | Met | Gly | Leu | Ile | Gln | Thr | Ala | Asp | Gln | Leu | Arg | Phe | Ser | Tyr | Leu | |
| | | | 260 | | | | | 265 | | | | | 270 | | | |
| gct | gtg | atc | gag | ggt | gca | aag | ttc | atc | atg | ggc | gac | tcg | tca | gtg | cag | 983 |
| Ala | Val | Ile | Glu | Gly | Ala | Lys | Phe | Ile | Met | Gly | Asp | Ser | Ser | Val | Gln | |
| | | 275 | | | | | 280 | | | | | 285 | | | | |
| gat | cag | tgg | aag | gag | ctt | tcc | cat | gaa | gac | ctg | gag | cct | ccc | cct | gag | 1031 |
| Asp | Gln | Trp | Lys | Glu | Leu | Ser | His | Glu | Asp | Leu | Glu | Pro | Pro | Pro | Glu | |
| | 290 | | | | | 295 | | | | | 300 | | | | | |
| cac | gtg | ccc | cca | cct | ccc | cgg | cca | ccc | aaa | cgc | aca | ttg | gag | cct | cac | 1079 |
| His | Val | Pro | Pro | Pro | Pro | Arg | Pro | Pro | Lys | Arg | Thr | Leu | Glu | Pro | His | |
| 305 | | | | | 310 | | | | | 315 | | | | | 320 | |
| aat | ggc | aag | tgc | aag | gag | ctc | ttc | tcc | aac | cac | cag | tgg | gtg | agc | gag | 1127 |
| Asn | Gly | Lys | Cys | Lys | Glu | Leu | Phe | Ser | Asn | His | Gln | Trp | Val | Ser | Glu | |
| | | | | 325 | | | | | 330 | | | | | 335 | | |
| gag | agc | tgt | gag | gat | gag | gac | atc | ctg | gcc | aga | gag | gaa | agc | aga | gcc | 1175 |
| Glu | Ser | Cys | Glu | Asp | Glu | Asp | Ile | Leu | Ala | Arg | Glu | Glu | Ser | Arg | Ala | |
| | | | 340 | | | | | 345 | | | | | 350 | | | |
| ccc | tca | att | gct | gtg | cac | agc | atg | agc | agt | atg | agt | caa | gac | act | gaa | 1223 |
| Pro | Ser | Ile | Ala | Val | His | Ser | Met | Ser | Ser | Met | Ser | Gln | Asp | Thr | Glu | |
| | | 355 | | | | | 360 | | | | | 365 | | | | |
| gtt | agg | aaa | cgg | atg | gtg | ggt | gga | ggt | ctt | caa | agt | gct | cag | gca | tct | 1271 |

-continued

| | |
|---|---|
| Val Arg Lys Arg Met Val Gly Gly Leu Gln Ser Ala Gln Ala Ser<br>370                           375                         380 | |
| gtc ccc act gag gaa gag ctg tcc cca acc gag gag gaa caa aag gca<br>Val Pro Thr Glu Glu Glu Leu Ser Pro Thr Glu Glu Glu Gln Lys Ala<br>385                         390                         395                       400 | 1319 |
| cac agg cca gtt cac tgg aag ccc ttc ctg gtc aac gtg tgc atg gcc<br>His Arg Pro Val His Trp Lys Pro Phe Leu Val Asn Val Cys Met Ala<br>                         405                         410                       415 | 1367 |
| acg gcc ctg gcg act ggc gcg tac ctc tgt tac cgg gta tgt ttt cac<br>Thr Ala Leu Ala Thr Gly Ala Tyr Leu Cys Tyr Arg Val Cys Phe His<br>                      420                       425                       430 | 1415 |
| tga cagactgctg tgaggcatga gcgtggtggg cgctgccact gcccaggtta | 1468 |
| ggatttggtc tgcggcgtct aacctggtgt agaagaaaca acagcttaca agcctgtggt | 1528 |
| ggaactggaa gggccagccc caggaggggc atctgtgcac tgggctttga aggagcccct | 1588 |
| ggtcccaaga acagagtcta atctcagggc cttaacctgt tcaggagaag tagaggaaat | 1648 |
| gccaaatact cttcttgctc tcacctcact cctccccttt ctctggttcg tttgttttg | 1708 |
| gaaaaaaaa aaaagaatt acaacacatt gttgttttta acatttataa aggcaggttt | 1768 |
| ttgttatttt tagagaaaac aaaagatgct aggcactggt gagattctct tgtgcccttt | 1828 |
| ggcatgtgat cagattcacg atttacgttt atttccgggg gagggtccca cctgtcagga | 1888 |
| ctgtaaagtt cctgctggct tggtcagccc cccacccccc caccccgag cttgcaggtg | 1948 |
| ccctgctgtg aggagagcag cagcagaggc tgccctgga cagaagccca gctctgcttc | 2008 |
| cctcaggtgt ccctgcgttt ccatcctcct tctttgtgac cgccatcttg cagatgaccc | 2068 |
| agtcctcagc accccacccc tgcagatggg tttctccgag ggcctgcctc agggtcatca | 2128 |
| gaggttggct gccagcttag agctggggct tccatttgat tggaaagtca ttactattct | 2188 |
| atgtagaagc cactccactg aggtgtaaag caagactcat aaaggaggag ccttggtgtc | 2248 |
| atggaagtca ctccgcgcgc aggacctgta acaacctctg aaacactcag tcctgctgca | 2308 |
| gtgacgtcct tgaaggcatc agacagatga tttgcagact gccaagactt gtcctgagcc | 2368 |
| gtgattttta gagtctggac tcatgaaaca ccgccgagcg cttactgtgc agcctctgat | 2428 |
| gctggttggc tgaggctgcg gggaggtgga cactgtgggt gcatccagtg cagttgcttt | 2488 |
| tgtgcagttg ggtccagcag cacagcccgc actccagcct cagctgcagg ccacagtggc | 2548 |
| catggaggcc gccagagcga gctggggtgg atgcttgttc acttggagca gccttcccag | 2608 |
| gacgtgcagc tcccttcctg ctttgtcctt ctgcttcctt ccctggagta gcaagcccac | 2668 |
| gagcaatcgt gaggggtgtg agggagctgc agaggcatca gagtggcctg cagcggcgtg | 2728 |
| aggccccttc ccctccgaca ccccctcca gaggagccgc tccactgtta tttattcact | 2788 |
| ttgcccacag acaccctga gtgagcacac cctgaaactg accgtgtaag gtgtcagcct | 2848 |
| gcacccagga ccgtcaggtg cagcaccggg tcagtcctag ggttgaggta ggactgacac | 2908 |
| agccactgtg tggctggtgc tggggcaggg gcaggagctg agggtcttag aagcaatctt | 2968 |
| caggaacaga caacagtggt gacatgtaaa gtccctgtgg ctactgatga catgtgtagg | 3028 |
| atgaaggctg gcctttctcc catgactttc tagatcccgt tccccgtctg ctttccctgt | 3088 |
| gagttagaaa acacacaggc tcctgtcctg gtggtgccgt gtgcttgaca tgggaaactt | 3148 |
| agatgcctgc tcactggcgg gcacctcggc atcgccacca ctcagagtga gagcagtgct | 3208 |
| gtccagtgcc gaggccgcct gactcccggc aggactcttc aggctctggc ctgccccagc | 3268 |
| acccccgct ggatctcaga cattccacac ccacacctca ttccctggac acttgggcaa | 3328 |

-continued

| | | |
|---|---|---|
| gcaggcccgc ccttccacct ctggggtcag cccctccatt ccgagttcac actgctctgg | 3388 |
| agcaggccag gaccggaagc aaggcagctg gtgaggagca ccctcctggg aacagtgtag | 3448 |
| gtgacagtcc tgagagtcag cttgctagcg ctgctggcac cagtcacctt gctcagaagt | 3508 |
| gtgtggctct tgaggctgaa gagactgatg atggtgctca tgactcttct gtgaggggaa | 3568 |
| cttgaccttc acattgggtg cttttttta aaataagcga aggcagctgg aactccagtc | 3628 |
| tgcctcttgc cagcacttca cattttgcct ttcacccaga gaagccagca cagagccact | 3688 |
| ggggaaggcg atggccttgc ctgcacaggc tgaggagatg gctcagccgg cgtccaggct | 3748 |
| gtgtctggag caggggtgc acagcagcct cacaggtggg ggcctcagag caggcgctgc | 3808 |
| cctgtcccct gccccgctgg aggcagcaaa gctgctgcat gccttaagtc aatacttact | 3868 |
| cagcagggcg ctctcgttct ctctctctct ctctctctct ctctctctct ctctctctct | 3928 |
| ctctctaaat ggccatagaa taaaccattt tacaaaaata aaagccaaca acaaagtgct | 3988 |
| ctggaatagc acctttgcag gagcgggggg tgtctcaggg tcttctgtga cctcaccgaa | 4048 |
| ctgtccgact gcaccgtttc caacttgtgt ctcactaatg ggtctgcatt agttgcaaca | 4108 |
| ataaatgttt ttaaagaac | 4127 |

<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11
cgagggtgca aagttcatca t                                              21

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12
ccaggtcttc atgggaaagc t                                              21

<210> SEQ ID NO 13
<211> LENGTH: 26
<212> TYPE: DNA
<213> ORGANISM: Artificial  Sequence
<220> FEATURE:
<223> OTHER INFORMATION: PCR Probe

<400> SEQUENCE: 13
cgactcgtca gtgcaggatc agtgga                                         26

<210> SEQ ID NO 14
<211> LENGTH: 23
<212> TYPE: DNA
<213> ORGANISM: Artificial Sequence
<220> FEATURE:
<223> OTHER INFORMATION: PCR Primer

<400> SEQUENCE: 14
tgttctagag acagccgcat ctt                                            23

<210> SEQ ID NO 15
<211> LENGTH: 21

```
<212> TYPE: DNA
<213> ORGANISM: Artificial Sequence
<220> FEATURE:
<223> OTHER INFORMATION: PCR Primer

<400> SEQUENCE: 15
caccgacctt caccatcttg t                                              21

<210> SEQ ID NO 16
<211> LENGTH: 24
<212> TYPE: DNA
<213> ORGANISM: Artificial Sequence
<220> FEATURE:
<223> OTHER INFORMATION: PCR Probe

<400> SEQUENCE: 16
ttgtgcagtg ccagcctcgt ctca                                           24

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
cttagccccg aggcccgccc                                                20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
ctcggcccac tgcgccgtct                                                20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
catgacgggc cagggcggct                                                20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
cccggacttg tcgatctgct                                                20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
```
ctggcttcat gtcggatatc                                                20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ttggccactc tacatgggaa                                                20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ggactgacgt ctctgtacct                                                20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
gatgtagttt aatccgacta                                                20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ctagcgttga tatagtcatt                                                20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
gggtaagaat gtaactcctt                                                20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
tgaccgcatg tgttaggcaa                                                20

<210> SEQ ID NO 28
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 28
ttttctgctc ccacaccatc                                               20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ctctgttgag catgacgaca                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gcgcatttta acgaaccttt                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
aaatttgtgt cttcaaagat                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
tgatatcttc agagatcaat                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tctagctgtc gcactgtata                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
agtttcttgg gttgtaaggt                                               20
```

```
<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gtggtatagt ggaaatgtaa                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
tgattcaggg actccaaagt                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ttgaaaagaa agttcaagaa                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gggctgagtg accctgactc                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gcagtgcacc acaacgggcc                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
aggttccaga cctgccgatg                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 41
agcaggaggc aggtatcagc                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gaagaagggt ctttcctctt                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
tctaacagca ctttcttgat                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
atcaacccca tccgaaactt                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gagaagcgca gctggtcggc                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
tttggcacct tcgatcacag                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
agctccttcc actgatcctg                                               20

<210> SEQ ID NO 48

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
tccaggattc gtttgggtgg                                                     20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
gaactccctg catttcccat                                                     20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ttccttcacc cactggtgat                                                     20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gtagggtgcg gcatttaagg                                                     20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
cagtgtcttg actcatgctt                                                     20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
gcctgggcac ctcgaagact                                                     20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ctcgtccttc tcgggcagtg                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
gggcttccag taactcagtg                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ccgtagccac gcacatgttg                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
tagcagaggt aagcgccggc                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ctatgtgttg ctgttgaaca                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ggaggtggag tggaggaggg                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ggctctgcgg gcagaggcgg                                              20

<210> SEQ ID NO 61
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 61
ccgcggcatg cctgctagtc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
tctctacgcg gtccggcggc                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
aagatgggtt ttagtgcaga                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
gtactctctt tcactctcct                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ggccccttcc ctctgcgccg                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
ctccaggagg gagccctggg                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
gggctgttgg cgtgcgccgc                                              20
```

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
tttaaataaa tatggagtgg                                                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
gttcaagaaa atgctagtgc                                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ttgataaagc ccttgatgca                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
atggcaaagc cttccattcc                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
gtcctccttc ccagtactgg                                                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ttacccacaa tatcactaaa                                                    20

<210> SEQ ID NO 74
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 74
attatatatt atagcattgt                                                      20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
tcacatcatg tttcttatta                                                      20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ataacaggga ggagaataag                                                      20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ttacatgcat tctaatacac                                                      20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
gatcaaagtt tctcatttca                                                      20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ggtcatgcac aggcaggttg                                                      20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
caacaggctt aggaaccaca                                                      20

```
<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
aactgcaccc tattgctgag                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gtcatgccag gaattagcaa                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
acaggctggg cctcaccagg                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
tgagttacag caagaccctg                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
gaatatggct tcccataccc                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ccctaaatca tgtccagagc                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 87
gacttggaat ggcggaggct                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
caaatcacgg tctgctcaag                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gaagtgtggt ttccagcagg                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
cctaaaggac cgtcacccag                                               20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gtgaaccggg acagagacgg                                               20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gccccacagg gtttgagggt                                               20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
cctttgcagg aagagtcgtg                                               20

<210> SEQ ID NO 94
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 94
aaagccactt aatgtggagg                                           20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
gtgaaaatgc tggcaagaga                                           20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tcagaatgct tacagcctgg                                           20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
caacctcccc agcagcggct                                           20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
tcgaggcccg tcgcccgcca                                           20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
cctcggccgt ccgccgcgct                                           20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
```

```
tcgatctgct cgaattcctt                                               20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
cctggtaaat agccgcccag                                               20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
tgtcgaatat cctggtaaat                                               20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
actggcttca tgtcgaatat                                               20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
aagtcactgg cttcatgtcg                                               20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
gaagtcactg gcttcatgtc                                               20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
ggaagtcact ggcttcatgt                                               20

<210> SEQ ID NO 107
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 107
gggaagtcac tggcttcatg                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
tgggaagtca ctggcttcat                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
atgggaagtc actggcttca                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
catgggaagt cactggcttc                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tttttgttct taggaagttt                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
cggtttttgt tcttaggaag                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
tccgactgtg gtcaaaaggg                                               20
```

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
ttaatccgac tgtggtcaaa                                                    20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
atagtcatta tcttcctgat                                                    20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
ttgatatagt cattatcttc                                                    20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
gcttcctcca ttttatcaa                                                     20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
ggccctgggt gaggatatag                                                    20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
cacaccatct cccagaagtg                                                    20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
tgctcccaca ccatctccca                                           20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
ctgctcccac accatctccc                                           20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
tctgctccca caccatctcc                                           20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
ttctgctccc acaccatctc                                           20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
cccctgctct tctgctccca                                           20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
atgcggttga gcatgaccac                                           20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
tttaacgagc ctttctccat                                           20

<210> SEQ ID NO 127

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
ttttcttctt tctgtggcca                                               20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
gaccatctct ttttcttctt                                               20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
tcagagatca gtgtcagctt                                               20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
cttgacatct tcagagatca                                               20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
taatatgact tgacatcttc                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
aactccaact gccgtactgt                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
```
tctctcgagc ctcctgggta                                               20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
ccaaagtcag gccaggtggt                                               20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
gggactccaa agtcaggcca                                               20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
agggactcca aagtcaggcc                                               20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
cagggactcc aaagtcaggc                                               20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
tcagggactc caaagtcagg                                               20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
ggtgactcag ggactccaaa                                               20

<210> SEQ ID NO 140
<211> LENGTH: 20
<212> TYPE: DNA

-continued

```
<213> ORGANISM: Artificial Sequence
<220> FEATURE:
<223> OTHER INFORMATION: Antisense Oligonucleotide

<400> SEQUENCE: 140
cctgactctc ggactttgaa                                               20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
gctgagtgag cctgactctc                                               20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
ccgtgctctg ggctgagtga                                               20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
aaggtccctg acctgccaat                                               20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
tctttcctct tgtccatcag                                               20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
gtctttcctc ttgtccatca                                               20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
ggtctttcct cttgtccatc                                               20
```

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
gggtctttcc tcttgtccat                                                     20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
aacagcactt tcttgatgtc                                                     20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
ggaacctgcg catctccaac                                                     20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
tggtcggccg tctggatgag                                                     20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
gagaagcgca gttggtcggc                                                     20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
aggtaggaga agcgcagttg                                                     20

<210> SEQ ID NO 153
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 153
gccaggtagg agaagcgcag                                           20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
agccaggtag gagaagcgca                                           20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
cagccaggta ggagaagcgc                                           20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
acagccaggt aggagaagcg                                           20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
cacagccagg taggagaagc                                           20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
tcacagccag gtaggagaag                                           20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
atcacagcca ggtaggagaa                                           20
```

```
<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
gatcacagcc aggtaggaga                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
cgatcacagc caggtaggag                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
tcgatcacag ccaggtagga                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
caccctcgat cacagccagg                                              20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
tccttccact gatcctgcac                                              20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
ctccttccac tgatcctgca                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 166
gctccttcca ctgatcctgc                                               20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
agctccttcc actgatcctg                                               20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
aagctccttc cactgatcct                                               20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
aaagctcctt ccactgatcc                                               20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
gaaagctcct tccactgatc                                               20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
ggaaagctcc ttccactgat                                               20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
gggaaagctc cttccactga                                               20

<210> SEQ ID NO 173
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 173
tgggaaagct ccttccactg                                           20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
tggccgggga ggtgggggca                                           20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
tgggtggccg gggaggtggg                                           20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
tgcgtttggg tggccgggga                                           20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
tgcacttgcc attgtgaggc                                           20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
acttcagtgt cttgactcat                                           20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
```
aacttcagtg tcttgactca                                      20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180
taacttcagt gtcttgactc                                      20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
ctaacttcag tgtcttgact                                      20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
gacagatgcc tgagcacttt                                      20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
gaccaggaag ggcttccagt                                      20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
tgaccaggaa gggcttccag                                      20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
ttgaccagga agggcttcca                                      20

<210> SEQ ID NO 186
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 186
gttgaccagg aagggcttcc                                           20

<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187
gcacacgttg accaggaagg                                           20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188
gaggtacgcg ccagtcgcca                                           20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
tacccggtaa cagaggtacg                                           20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
agtgaaaaca tacccggtaa                                           20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
caaatcctaa cctgggcagt                                           20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
ttccagttcc accacaggct                                           20
```

```
<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193
ccagtgcaca gatgccctc                                                 20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
acaggttaag gccctgagat                                                20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
gcctagcatc ttttgttttc                                                20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
aagccagcag gaactttaca                                                20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
gggacacctg agggaagcag                                                20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
ggtcatctgc aagatggcgg                                                20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 199
gccaacctct gatgaccctg                                          20

<210> SEQ ID NO 200
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 200
tggaagcccc agctctaagc                                          20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
tagtaatgac tttccaatca                                          20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202
tgagtcttgc tttacacctc                                          20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
cctgcgcgcg gagtgacttc                                          20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
aggacgtcac tgcagcagga                                          20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
tcaggacaag tcttggcagt                                          20

<210> SEQ ID NO 206
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
gaggctgcac agtaagcgct                                              20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
tcagccaacc agcatcagag                                              20

<210> SEQ ID NO 208
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 208
acccacagtg tccacctccc                                              20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
agtgcgggct gtgctgctgg                                              20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
cagctcgctc tggcggcctc                                              20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
aggaagggag ctgcacgtcc                                              20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
```

```
ccctcacgat tgctcgtggg                                            20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 213
cagtggagcg gctcctctgg                                            20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
caggctgaca ccttacacgg                                            20

<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
gtcctacctc aaccctagga                                            20

<210> SEQ ID NO 216
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 216
ctgccccagc accagccaca                                            20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
attgcttcta agaccctcag                                            20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
ttacatgtca ccactgttgt                                            20

<210> SEQ ID NO 219
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 219
tacacatgtc atcagtagcc                                                    20

<210> SEQ ID NO 220
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220
ttttctaact cacagggaaa                                                    20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221
gtgcccgcca gtgagcaggc                                                    20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222
cggcctcggc actggacagc                                                    20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
gtggaatgtc tgagatccag                                                    20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
agggcgggcc tgcttgccca                                                    20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
cggtcctggc ctgctccaga                                                    20
```

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
tacactgttc ccaggagggt                                           20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
tggtgccagc agcgctagca                                           20

<210> SEQ ID NO 228
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 228
cagtctcttc agcctcaaga                                           20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
aagagtcatg agcaccatca                                           20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
tgaaggtcaa gttcccctca                                           20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
ctggcaagag gcagactgga                                           20

<210> SEQ ID NO 232
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 232
ggctctgtgc tggcttctct                                              20

<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 233
gccatctcct cagcctgtgc                                              20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234
agcgcctgct ctgaggcccc                                              20

<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235
tgctgagtaa gtattgactt                                              20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236
ctatggccat ttagagagag                                              20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
tggtttattc tatggccatt                                              20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
cgctcctgca aagtgctat                                               20
```

```
<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239
gttggaaacg gtgcagtcgg                                              20

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240
atttattgtt gcaactaatg                                              20

<210> SEQ ID NO 241
<211> LENGTH: 2346
<212> TYPE: DNA
<213> ORGANISM: Mus musculus
<220> FEATURE:
<221> NAME/KEY: CDS
<222> LOCATION: (710)...(2008)

<400> SEQUENCE: 241
gaattcggga tccttttgca cattcctagt tagcagtgca tactcatcag actggagatg    60
tttaatgaca tcagggaacc aaacggacaa cccatagtac ccgaagacag ggtgaaccag   120
acaatcgtaa gcttgatggt gttttccctg actgggtagt tgaagcatct catgaatgtc   180
agccaaattc cgtacagttc ggtgcggatc cgaacgaaac acctcctgta ccaggttccc   240
gtgtcgctct caatttcaat cagctcatct atttgtttgg gagtcttgat tttatttacc   300
gtgaagacct tctctggctg gccccgggct ctcatgttgg tgtcatgaat taacttcaga   360
atcatccagg cttcatcatg ttttcccacc tccagcaaga accgagggct ttctggcatg   420
aaggtgagag ccaccacaga ggagacgcat gggagcgcac agacgatgac gaagacgcgc   480
cacgtgtgga actggtaggc tgaacccatg ctgaagctcc accgtagtg  gggaatgatg   540 gcccaggcat ggcggaggct agatgccgcc aatcatccag aacatgcaga agccgctgct   600
ggggagcttg gggctgcggt ggtggcgggt gacgggcttc gggacgcgga gcgacgcggc   660
ctagcgcggc ggacggccgt gggaactcgg gcagccgacc cgtcccgcc atg gag atg  718
                                                     Met Glu Met
                                                      1 gag aag gag ttc gag gag atc gac aag gct ggg aac tgg gcg gct att     766
Glu Lys Glu Phe Glu Glu Ile Asp Lys Ala Gly Asn Trp Ala Ala Ile
       5                  10                  15 tac cag gac att cga cat gaa gcc agc gac ttc cca tgc aaa gtc gcg     814
Tyr Gln Asp Ile Arg His Glu Ala Ser Asp Phe Pro Cys Lys Val Ala
 20                  25                  30                  35 aag ctt cct aag aac aaa aac cgg aac agg tac cga gat gtc agc cct     862
Lys Leu Pro Lys Asn Lys Asn Arg Asn Arg Tyr Arg Asp Val Ser Pro
                 40                  45                  50 ttt gac cac agt cgg att aaa ttg cac cag gaa gat aat gac tat atc     910
Phe Asp His Ser Arg Ile Lys Leu His Gln Glu Asp Asn Asp Tyr Ile
             55                  60                  65 aat gcc agc ttg ata aaa atg gaa gaa gcc cag agg agc tat att ctc     958
Asn Ala Ser Leu Ile Lys Met Glu Glu Ala Gln Arg Ser Tyr Ile Leu
         70                  75                  80
```

-continued

| | |
|---|---|
| acc cag ggc cct tta cca aac aca tgt ggg cac ttc tgg gag atg gtg<br>Thr Gln Gly Pro Leu Pro Asn Thr Cys Gly His Phe Trp Glu Met Val<br>85                        90                            95 | 1006 |
| tgg gag cag aag agc agg ggc gtg gtc atg ctc aac cgc atc atg gag<br>Trp Glu Gln Lys Ser Arg Gly Val Val Met Leu Asn Arg Ile Met Glu<br>100                   105                   110                 115 | 1054 |
| aaa ggc tcg tta aaa tgt gcc cag tat tgg cca cag caa gaa gaa aag<br>Lys Gly Ser Leu Lys Cys Ala Gln Tyr Trp Pro Gln Gln Glu Glu Lys<br>                 120                 125                 130 | 1102 |
| gag atg gtc ttt gat gac aca ggt ttg aag ttg aca cta atc tct gaa<br>Glu Met Val Phe Asp Asp Thr Gly Leu Lys Leu Thr Leu Ile Ser Glu<br>             135                 140                 145 | 1150 |
| gat gtc aag tca tat tac aca gta cga cag ttg gag ttg gaa aac ctg<br>Asp Val Lys Ser Tyr Tyr Thr Val Arg Gln Leu Glu Leu Glu Asn Leu<br>150                        155                   160 | 1198 |
| act acc aag gag act cga gag atc ctg cat ttc cac tac acc aca tgg<br>Thr Thr Lys Glu Thr Arg Glu Ile Leu His Phe His Tyr Thr Thr Trp<br>165                        170                   175 | 1246 |
| cct gac ttt gga gtc ccc gag tca ccg gct tct ttc ctc aat ttc ctt<br>Pro Asp Phe Gly Val Pro Glu Ser Pro Ala Ser Phe Leu Asn Phe Leu<br>180                        185                 190                 195 | 1294 |
| ttc aaa gtc cga gag tca ggc tca ctc agc ctg gag cat ggc ccc att<br>Phe Lys Val Arg Glu Ser Gly Ser Leu Ser Leu Glu His Gly Pro Ile<br>                 200                 205                 210 | 1342 |
| gtg gtc cac tgc agc gcc ggc atc ggg agg tca ggg acc ttc tgt ctg<br>Val Val His Cys Ser Ala Gly Ile Gly Arg Ser Gly Thr Phe Cys Leu<br>             215                 220                 225 | 1390 |
| gct gac acc tgc ctc tta ctg atg gac aag agg aaa gac cca tct tcc<br>Ala Asp Thr Cys Leu Leu Leu Met Asp Lys Arg Lys Asp Pro Ser Ser<br>             230                 235                 240 | 1438 |
| gtg gac atc aag aaa gta ctg ctg gag atg cgc agg ttc cgc atg ggg<br>Val Asp Ile Lys Lys Val Leu Leu Glu Met Arg Arg Phe Arg Met Gly<br>245                        250                   255 | 1486 |
| ctc atc cag act gcc gac cag ctg cgc ttc tcc tac ctg gct gtc atc<br>Leu Ile Gln Thr Ala Asp Gln Leu Arg Phe Ser Tyr Leu Ala Val Ile<br>260                        265                   270                 275 | 1534 |
| gag ggc gcc aag ttc atc atg ggc gac tcg tca gtg cag gat cag tgg<br>Glu Gly Ala Lys Phe Ile Met Gly Asp Ser Ser Val Gln Asp Gln Trp<br>                 280                 285                 290 | 1582 |
| aag gag ctc tcc cgg gag gat cta gac ctt cca ccc gag cac gtg ccc<br>Lys Glu Leu Ser Arg Glu Asp Leu Asp Leu Pro Pro Glu His Val Pro<br>             295                 300                 305 | 1630 |
| cca cct ccc cgg cca ccc aaa cgc aca ctg gag cct cac aac ggg aag<br>Pro Pro Pro Arg Pro Pro Lys Arg Thr Leu Glu Pro His Asn Gly Lys<br>310                        315                   320 | 1678 |
| tgc aag gag ctc ttc tcc agc cac cag tgg gtg agc gag gag acc tgt<br>Cys Lys Glu Leu Phe Ser Ser His Gln Trp Val Ser Glu Glu Thr Cys<br>325                        330                   335 | 1726 |
| ggg gat gaa gac agc ctg gcc aga gag gaa ggc aga gcc cag tca agt<br>Gly Asp Glu Asp Ser Leu Ala Arg Glu Glu Gly Arg Ala Gln Ser Ser<br>340                        345                   350                 355 | 1774 |
| gcc atg cac agc gtg agc agc atg agt cca gac act gaa gtt agg aga<br>Ala Met His Ser Val Ser Ser Met Ser Pro Asp Thr Glu Val Arg Arg<br>             360                 365                 370 | 1822 |
| cgg atg gtg ggt gga ggt ctt caa agt gct cag gcg tct gtc ccc acc<br>Arg Met Val Gly Gly Leu Gln Ser Ala Gln Ala Ser Val Pro Thr<br>             375                 380                 385 | 1870 |
| gag gaa gag ctg tcc tcc act gag gag gaa cac aag gca cat tgg cca<br>Glu Glu Glu Leu Ser Ser Thr Glu Glu Glu His Lys Ala His Trp Pro<br>390                        395                   400 | 1918 |

-continued

```
agt cac tgg aag ccc ttc ctg gtc aat gtg tgc atg gcc acg ctc ctg      1966
Ser His Trp Lys Pro Phe Leu Val Asn Val Cys Met Ala Thr Leu Leu
    405                 410                 415 gcc acc ggc gcg tac ttg tgc tac cgg gtg tgt ttt cac tga              2008
Ala Thr Gly Ala Tyr Leu Cys Tyr Arg Val Cys Phe His  *
420                 425                 430 cagactggga ggcactgcca ctgcccagct taggatgcgg tctgcggcgt ctgacctggt    2068
gtagagggaa caacaactcg caagcctgct ctggaactgg aagggcctgc cccaggaggg    2128
tattagtgca ctgggctttg aaggagcccc tggtcccacg aacagagtct aatctcaggg    2188
ccttaacctg ttcaggagaa gtagaggaaa tgccaaatac tcttcttgct ctcacctcac    2248
tcctcccctt tctctgattc atttgttttt ggaaaaaaaa aaaaaaagaa ttacaacaca    2308
ttgttgtttt taacatttat aaaggcaggc ccgaattc                            2346
```

<210> SEQ ID NO 242
<211> LENGTH: 20
<212> TYPE: DNA
<213> ORGANISM: Artificial Sequence
<220> FEATURE:
<221> NAME/KEY: unsure
<222> LOCATION: (1)..(20)
<223> OTHER INFORMATION: Antisense Oligonucleotide

<400> SEQUENCE: 242
nnnnnnnnnn nnnnnnnnnn                                                 20

ANTISENSE MODULATION OF PTP1B EXPRESSION

This application is a continuation-in-part of U.S. patent application Ser. No. 09/487,368, filed Jan. 18, 2000.

FIELD OF THE INVENTION

The present invention provides compositions and methods for modulating the expression of PTP1B. In particular, this invention relates to compounds, particularly antisense oligonucleotides, specifically hybridizable with nucleic acids encoding PTP1B. Such oligonucleotides have been shown to modulate the expression of PTP1B.

BACKGROUND OF THE INVENTION

The process of phosphorylation, defined as the attachment of a phosphate moiety to a biological molecule through the action of enzymes called kinases, represents one course by which intracellular signals are propagated resulting finally in a cellular response. Within the cell, proteins can be phosphorylated on serine, threonine or tyrosine residues and the extent of phosphorylation is regulated by the opposing action of phosphatases, which remove the phosphate moieties. While the majority of protein phosphorylation within the cell is on serine and threonine residues, tyrosine phosphorylation is modulated to the greatest extent during oncogenic transformation and growth factor stimulation (Zhang, Crit. Rev. Biochem. Mol. Biol., 1998, 33, 1–52).

Because phosphorylation is such a ubiquitous process within cells and because cellular phenotypes are largely influenced by the activity of these pathways, it is currently believed that a number of disease states and/or disorders are a result of either aberrant activation of, or functional mutations in, kinases and phosphatases. Consequently, considerable attention has been devoted recently to the characterization of tyrosine kinases and tyrosine phosphatases.

PTP1B (also known as protein phosphatase 1B and PTPN1) is an endoplasmic reticulum (ER)-associated enzyme originally isolated as the major protein tyrosine phosphatase of the human placenta (Tonks et al., J. Biol. Chem., 1988, 263, 6731–6737; Tonks et al., J. Biol. Chem., 1988, 263, 6722–6730).

An essential regulatory role in signaling mediated by the insulin receptor has been established for PTP1B. PTP1B interacts with and dephosphorylates the activated insulin receptor both in vitro and in intact cells resulting in the downregulation of the signaling pathway (Goldstein et al., Mol. Cell. Biochem., 1998, 182, 91–99; Seely et al., Diabetes, 1996, 45, 1379–1385). In addition, PTP1B modulates the mitogenic actions of insulin (Goldstein et al., Mol. Cell. Biochem., 1998, 182, 91–99). In rat adipose cells overexpressing PTP1B, the translocation of the GLUT4 glucose transporter was inhibited, implicating PTP1B as a negative regulator of glucose transport as well (Chen et al., J. Biol. Chem., 1997, 272, 8026–8031).

Mouse knockout models lacking the PTP1B gene also point toward the negative regulation of insulin signaling by PTP1B. Mice harboring a disrupted PTP1B gene showed increased insulin sensitivity, increased phosphorylation of the insulin receptor and when placed on a high-fat diet, PTP1B −/− mice were resistant to weight gain and remained insulin sensitive (Elchebly et al., Science, 1999, 283, 1544–1548). These studies clearly establish PTP1B as a therapeutic target in the treatment of diabetes and obesity.

PTP1B, which is differentially regulated during the cell cycle (Schievella et al., Cell. Growth Differ., 1993, 4, 239–246), is expressed in insulin sensitive tissues as two different isoforms that arise from alternate splicing of the pre-mRNA (Shifrin and Neel, J. Biol. Chem., 1993, 268, 25376–25384). It was recently demonstrated that the ratio of the alternatively spliced products is affected by growth factors such as insulin and differs in various tissues examined (Sell and Reese, Mol. Genet. Metab., 1999, 66, 189–192). In these studies it was also found that the levels of the variants correlated with the plasma insulin concentration and percentage body fat and may therefore be used as a biomarker for patients with chronic hyperinsulinemia or type 2 diabetes.

Liu and Chernoff have shown that PTP1B binds to and serves as a substrate for the epidermal growth factor receptor (EGFR) (Liu and Chernoff, i Biochem. J., 1997, 327, 139–145). Furthermore, in A431 human epidermoid carcinoma cells, PT1B was found to be inactivated by the presence of $H_2O_2$ generated by the addition of EGF. These studies indicate that PTP1B can be negatively regulated by the oxidation state of the cell, which is often deregulated during tumorigenesis (Lee et al., J. Biol. Chem., 1998, 273, 15366–15372).

Overexpression of PTP1B has been demonstrated in malignant ovarian cancers and this correlation was accompanied by a concomitant increase in the expression of the associated growth factor receptor (Wiener et al., Am. J. Obstet. Gynecol., 1994, 170, 1177–1183).

PTP1B has been shown to suppress transformation in NIH3T3 cells induced by the neu oncogene (Brown-Shimer et al., Cancer Res., 1992, 52, 478–482), as well as in rat 3Y1 fibroblasts induced by v-srk, v-src, and v-ras (Liu et al., Mol. Cell. Biol., 1998, 18, 250–259) and rat-1 fibroblasts induced by bcr-abl (LaMontagne et al., Proc. Natl. Acad. Sci. U. S. A., 1998, 95, 14094–14099). It has also been shown that PTP1B promotes differentiation of K562 cells, a chronic myelogenous leukemia cell line, in a similar manner as does an inhibitor of the bcr-abl oncoprotein. These studies describe the possible role of PTP1B in controlling the pathogenesis of chronic myeloid leukemia (LaMontagne et al., Proc. Natl. Acad. Sci. U. S. A., 1998, 95, 14094–14099).

PTP1B negatively regulates integrin signaling by interacting with one or more adhesion-dependent signaling components and repressing integrin-mediated MAP kinase activation (Liu et al., Curr. Biol., 1998, 8, 173–176). Other studies designed to study integrin signaling, using a catalytically inactive form of PTP1B, have shown that PTP1B regulates cadherin-mediated cell adhesion (Balsamo et al., J. Cell. Biol., 1998, 143, 523–532) as well as cell spreading, focal adhesion and stress fiber formation and tyrosine phosphorylation (Arregui et al., J. Cell. Biol., 1998, 143, 861–873).

Currently, therapeutic agents designed to inhibit the synthesis or action of PTP1B include small molecules (Ham et al., Bioorg. Med. Chem. Lett., 1999, 9, 185–186; Skorey et al., J. Biol. Chem., 1997, 272, 22472–22480; Taing et al., Biochemistry, 1999, 38, 3793–3803; Taylor et al., Bioorg. Med. Chem., 1998, 6, 1457–1468; Wang et al., Bioorg. Med. Chem. Lett., 1998, 8, 345–350; Wang et al., Biochem. Pharmacol., 1997, 54, 703–711; Yao et al., Bioorg. Med. Chem., 1998, 6, 1799–1810) and peptides (Chen et al., Biochemistry, 1999, 38, 384–389; Desmarais et al., Arch. Biochem. Biophys., 1998, 354, 225–231; Roller et al., Bioorg. Med. Chem. Lett., 1998, 8, 2149–2150). In addition, disclosed in the PCT publication WO 97/32595 are phosphopeptides and antibodies that inhibit the association of PTP1B with the activated insulin receptor for the treatment of disorders associated with insulin resistance. Antisense nucleotides against PTP1B are also generally disclosed (Olefsky, 1997).

There remains a long felt need for additional agents capable of effectively inhibiting PTP1B function and antisense technology is emerging as an effective means for reducing the expression of specific gene products. This technology may therefore prove to be uniquely useful in a number of therapeutic, diagnostic, and research applications for the modulation of PTP1B expression.

The present invention, therefore, provides compositions and methods for modulating PTP1B expression, including modulation of the alternatively spliced form of PTP1B.

SUMMARY OF THE INVENTION

The present invention is directed to antisense compounds, particularly oligonucleotides, which are targeted to a nucleic acid encoding PTP1B, and which modulate the expression of PTP1B. Pharmaceutical and other compositions comprising the antisense compounds of the invention are also provided. Further provided are methods of modulating the expression of PTP1B in cells or tissues comprising contacting said cells or tissues with one or more of the antisense compounds or compositions of the invention. Further provided are methods of treating an animal, particularly a human, suspected of having or being prone to a disease or condition associated with expression of PTP1B by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding PTP1B, ultimately modulating the amount of PTP1B produced. This is accomplished by providing antisense compounds which specifically hybridize with one or more nucleic acids encoding PTP1B. As used herein, the terms "target nucleic acid" and "nucleic acid encoding PTP1B" encompass DNA encoding PTP1B, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of PTP1B. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding PTP1B. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding PTP1B, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S.: U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S.: U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Most preferred embodiments of the invention are oligonucleotides with phosphorothioate backbones and oligonucleosides with heteroatom backbones, and in particular $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$ and $-O-N(CH_3)-CH_2-CH_2-$ [wherein the native phosphodiester backbone is represented as $-O-P-O-CH_2-$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S—or N-alkynyl; or o-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$ and $O(CH_2)_n ON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—$CH_2CH_2OCH_3$, also known as 2'—O—(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'—O—$CH_2$—O—$CH_2$—$N(CH_3)_2$, also described in examples hereinbelow.

Other preferred modifications include 2'-methoxy (2'—O—$CH_3$), 2'-aminopropoxy (2'—O$CH_2CH_2CH_2NH_2$) and 2'-fluoro (2'—F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S.: U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering,* pages 858–859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications,* pages 289–302, Crooke, S. T. and Lebleu, B. , ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications, CRC Press,* Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S.: U.S. Pat. Nos: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al., *Ann. N. Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937).

Representative United States patents that teach the preparation of such oligonucleotide conjugates include, but are not limited to, U.S.: U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S.: U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S.: U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of PTP1B is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding PTP1B, enabling sandwich and other assays to easily be constructed to exploit this fact.

Hybridization of the antisense oligonucleotides of the invention with a nucleic acid encoding PTP1B can be detected by means known in the art. Such means may include conjugation of an enzyme to the oligonucleotide, radiolabelling of the oligonucleotide or any other suitable detection means. Kits using such detection means for detecting the level of PTP1B in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolid.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms,* Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in *Pharmaceutical Dosage Forms,* Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,* Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms,* Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems,* Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences,* Mack Publishing Co., Easton, Pa, 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms,* Lieberman, Rieger and Banker (Eds.), 1988, Marcel Dekker, Inc., New York, N.Y., volume 1, p. 245; Block, in *Pharmaceutical Dosage Forms,* Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765). various liposomes comprising one or more glycolipids are known in the art. Papahadjopoulos et al. (*Ann. N. Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms,* Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., *J. Pharm. Pharmacol.,* 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy,* 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me—C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 5 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-acetyl-2'-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine 85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1

L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160 ° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethylazodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O-$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2
Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O—Me]-[2'-deoxy]-[2'-O—Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to 1/2 volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]--[2'-deoxy]--[2'-O-(Methoxyethyl)] Chimeric Phosphorothioate Oligonucleotides

[2'-O-(2-methoxyethyl)]--[2'-deoxy]--[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl) Phosphodiester] Chimeric Oligonucleotides

[2'-O-(2-methoxyethyl phosphodiester]--[2'-deoxy phosphorothioate]--[2'-O-(methoxyethyl)phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.
T-24 Cells The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.
A549 Cells The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

PC-12 Cells

The rat neuronal cell line PC-12 was obtained from the American Type Culure Collection (Manassas, Va.). PC-12 cells were routinely cultured in DMEM, high glucose (Gibco/Life Technologies, Gaithersburg, Md.) supplemented with 10% horse serum+5% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 20000 cells/well for use in RT-PCR analysis.

For Northern blotting or other analysis, cells may be seeded onto 100 mm or other standard tissue culture plates and treated similarly, using appropriate volumes of medium and oligonucleotide.

Treatment with Antisense Compounds

When cells reached 80% confluency, they were treated with oligonucleotide. For cells grown in 96-well plates, wells were washed once with 200 $\mu$L OPTI-MEM™-1 reduced-serum medium (Gibco BRL) and then treated with 130 $\mu$L of OPTI-MEM™-1 containing 3.75 $\mu$g/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 5770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of PTP1B Expression

Antisense modulation of PTP1B expression can be assayed in a variety of ways known in the art. For example, PTP1B mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed as multiplexable. Other methods of PCR are also known in the art.

Protein levels of PTP1B can be quantitated in a variety of ways well known in the art, such as immunoprecipitation, Western blot analysis (immunoblotting), ELISA or fluorescence-activated cell sorting (FACS). Antibodies directed to PTP1B can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11
Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12
Total RNA Isolation

Total mRNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13
Real-time Quantitative PCR Analysis of PTP1B mRNA Levels

Quantitation of PTP1B mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 μL PCR cocktail (1×TAQMAN™ buffer A, 5.5 mM MgCl$_2$, 300 μM each of DATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL poly(A) mRNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Probes and primers to human PTP1B were designed to hybridize to a human PTP1B sequence, using published sequence information (GenBank accession number M31724, incorporated herein as SEQ ID NO:3). For human PTP1B the PCR primers were:

forward primer: GGAGTTCGAGCAGATCGACAA (SEQ ID NO: 4)
reverse primer: GGCCACTCTACATGGGAAGTC (SEQ ID NO: 5) and the PCR probe was: FAM-AGCTGGGCGGCCATTTACCAGGAT-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

forward primer: GAAGGTGAAGGTCGGAGTC (SEQ ID NO: 7)
reverse primer: GAAGATGGTGATGGGATTTC (SEQ ID NO: 8) and the PCR probe was: 5' JOE-CAAGCTTCCCGTTCTCAGCC- TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to rat PTP1B were designed to hybridize to a rat PTP1B sequence, using published sequence information (GenBank accession number M33962, incorporated herein as SEQ ID NO:10). For rat PTP1B the PCR primers were:
forward primer: CGAGGGTGCAAAGTTCATCAT (SEQ ID NO:11)
reverse primer: CCAGGTCTTCATGGGAAAGCT (SEQ ID NO: 12) and the PCR probe was: FAM-CGACTCGTCAGTGCAGGATCAGTGGA-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For rat GAPDH the PCR primers were:
forward primer: TGTTCTAGAGACAGCCGCATCTT (SEQ ID NO: 14)
reverse primer: CACCGACCTTCACCATCTTGT (SEQ ID NO: 15) and the PCR probe was: 5' JOE-TTGTGCAGTGCCAGCCTCGTCTCA- TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of PTP1B mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human PTP1B, a human PTP1B specific probe was prepared by PCR using the forward primer GGAGTTCGAGCAGATCGACAA (SEQ ID NO: 4) and the reverse primer GGCCACTCTACATGGGAAGTC (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect rat PTP1B, a rat PTP1B specific probe was prepared by PCR using the forward primer CGAGGGTGCAAAGTTCATCAT (SEQ ID NO:11) and the reverse primer CCAGGTCTTCATGGGAAAGCT (SEQ ID NO: 12). To normalize for variations in loading and transfer efficiency membranes were stripped and probed for rat glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human PTP1B Expression by Chimeric Phosphorothioate Oligonucleotides Having 2'-MOE Wings and a Deoxy Gap In accordance with the present invention, a series of oligonucleotides were designed to target different regions of the human PTP1B RNA, using published sequences (GenBank accession number M31724, incorporated herein as SEQ ID NO: 3). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human PTP1B mRNA levels by quantitative real-time PCR as described in other examples herein. Data are averages from two experiments. If present, "N.D." indicates "no data".

TABLE 1

Inhibition of human PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 107769 | 5' UTR | 3 | 1 | cttagccccgaggcccgccc | 0 | 17 |
| 107770 | 5' UTR | 3 | 41 | ctcggcccactgcgccgtct | 58 | 18 |
| 107771 | Start Codon | 3 | 74 | catgacgggccagggcggct | 60 | 19 |
| 107772 | Coding | 3 | 113 | cccggacttgtcgatctgct | 95 | 20 |
| 107773 | Coding | 3 | 154 | ctggcttcatgtcggatatc | 88 | 21 |
| 107774 | Coding | 3 | 178 | ttggccactctacatgggaa | 77 | 22 |
| 107775 | Coding | 3 | 223 | ggactgacgtctctgtacct | 75 | 23 |
| 107776 | Coding | 3 | 252 | gatgtagtttaatccgacta | 82 | 24 |
| 107777 | Coding | 3 | 280 | ctagcgttgatatagtcatt | 29 | 25 |
| 107778 | Coding | 3 | 324 | gggtaagaatgtaactcctt | 86 | 26 |
| 107779 | Coding | 3 | 352 | tgaccgcatgtgttaggcaa | 75 | 27 |
| 107780 | Coding | 3 | 381 | ttttctgctcccacaccatc | 30 | 28 |
| 107781 | Coding | 3 | 408 | ctctgttgagcatgacgaca | 78 | 29 |
| 107782 | Coding | 3 | 436 | gcgcattttaacgaaccttt | 83 | 30 |
| 107783 | Coding | 3 | 490 | aaatttgtgtcttcaaagat | 0 | 31 |
| 107784 | Coding | 3 | 519 | tgatatcttcagagatcaat | 57 | 32 |
| 107785 | Coding | 3 | 547 | tctagctgtcgcactgtata | 74 | 33 |
| 107786 | Coding | 3 | 575 | agtttcttgggttgtaaggt | 33 | 34 |
| 107787 | Coding | 3 | 604 | gtggtatagtggaaatgtaa | 51 | 35 |
| 107788 | Coding | 3 | 632 | tgattcagggactccaaagt | 55 | 36 |
| 107789 | Coding | 3 | 661 | ttgaaaagaaagttcaagaa | 17 | 37 |
| 107790 | Coding | 3 | 688 | gggctgagtgaccctgactc | 61 | 38 |
| 107791 | Coding | 3 | 716 | gcagtgcaccacaacgggcc | 81 | 39 |
| 107792 | Coding | 3 | 744 | aggttccagacctgccgatg | 81 | 40 |
| 107793 | Coding | 3 | 772 | agcaggaggcaggtatcagc | 2 | 41 |
| 107794 | Coding | 3 | 799 | gaagaagggtctttcctctt | 53 | 42 |
| 107795 | Coding | 3 | 826 | tctaacagcactttcttgat | 18 | 43 |
| 107796 | Coding | 3 | 853 | atcaacccatccgaaactt | 0 | 44 |
| 107797 | Coding | 3 | 880 | gagaagcgcagctggtcggc | 82 | 45 |
| 107798 | Coding | 3 | 908 | tttggcaccttcgatcacag | 62 | 46 |
| 107799 | Coding | 3 | 952 | agctccttccactgatcctg | 70 | 47 |
| 107800 | Coding | 3 | 1024 | tccaggattcgtttgggtgg | 72 | 48 |
| 107801 | Coding | 3 | 1052 | gaactccctgcatttcccat | 68 | 49 |
| 107802 | Coding | 3 | 1079 | ttccttcacccactggtgat | 40 | 50 |
| 107803 | Coding | 3 | 1148 | gtagggtgcggcatttaagg | 0 | 51 |
| 107804 | Coding | 3 | 1176 | cagtgtcttgactcatgctt | 75 | 52 |
| 107805 | Coding | 3 | 1222 | gcctgggcacctcgaagact | 67 | 53 |
| 107806 | Coding | 3 | 1268 | ctcgtccttctcgggcagtg | 37 | 54 |

TABLE 1-continued

Inhibition of human PTP1B mRNA levels by chimeric phosphorothioate oligonucleotides having 2'-MOE wings and a deoxy gap

| ISIS # | RE-GION | TARGET SEQ ID NO | TARGET SITE | SEQUENCE | % INHIB | SEQ ID NO |
|---|---|---|---|---|---|---|
| 107807 | Coding | 3 | 1295 | gggcttccagtaactcagtg | 73 | 55 |
| 107808 | Coding | 3 | 1323 | ccgtagccacgcacatgttg | 80 | 56 |
| 107809 | Coding | 3 | 1351 | tagcagaggtaagcgccygc | 72 | 57 |
| 107810 | Stop Codon | 3 | 1379 | ctatgtgttgctgttgaaca | 85 | 58 |
| 107811 | 3' UTR | 3 | 1404 | ggaggtggagtggaggaggg | 51 | 59 |
| 107812 | 3' UTR | 3 | 1433 | ggctctgcgggcagaggcgg | 81 | 60 |
| 107813 | 3' UTR | 3 | 1460 | ccgcggcatgcctgctagtc | 84 | 61 |
| 107814 | 3' UTR | 3 | 1489 | tctctacgcggtccggcggc | 84 | 62 |
| 107815 | 3' UTR | 3 | 1533 | aagatgggttttagtgcaga | 65 | 63 |
| 107816 | 3' UTR | 3 | 1634 | gtactctctttcactctcct | 69 | 64 |
| 107817 | 3' UTR | 3 | 1662 | ggccccttccctctgcgccg | 59 | 65 |
| 107818 | 3' UTR | 3 | 1707 | ctccaggagggagccctggg | 57 | 66 |
| 107819 | 3' UTR | 3 | 1735 | gggctgttggcgtgcgccgc | 54 | 67 |
| 107820 | 3' UTR | 3 | 1783 | tttaaataaatatggagtgg | 0 | 68 |
| 107821 | 3' UTR | 3 | 1831 | gttcaagaaaatgctagtgc | 69 | 69 |
| 107822 | 3' UTR | 3 | 1884 | ttgataaagcccttgatgca | 74 | 70 |
| 107823 | 3' UTR | 3 | 1936 | atggcaaagccttccattcc | 26 | 71 |
| 107824 | 3' UTR | 3 | 1973 | gtcctccttcccagtactgg | 60 | 72 |
| 107825 | 3' UTR | 3 | 2011 | ttacccacaatatcactaaa | 39 | 73 |
| 107826 | 3' UTR | 3 | 2045 | attatatattatagcattgt | 24 | 74 |
| 107827 | 3' UTR | 3 | 2080 | tcacatcatgttttcttatta | 48 | 75 |
| 107828 | 3' UTR | 3 | 2115 | ataacagggaggagaataag | 0 | 76 |
| 107829 | 3' UTR | 3 | 2170 | ttacatgcattctaatacac | 21 | 77 |
| 107830 | 3' UTR | 3 | 2223 | gatcaaagtttctcatttca | 81 | 78 |
| 107831 | 3' UTR | 3 | 2274 | ggtcatgcacaggcaggttg | 82 | 79 |
| 107832 | 3' UTR | 3 | 2309 | caacaggcttaggaaccaca | 65 | 80 |
| 107833 | 3' UTR | 3 | 2344 | aactgcaccctattgctgag | 61 | 81 |
| 107834 | 3' UTR | 3 | 2380 | gtcatgccaggaattagcaa | 0 | 82 |
| 107835 | 3' UTR | 3 | 2413 | acaggctgggcctcaccagg | 58 | 83 |
| 107836 | 3' UTR | 3 | 2443 | tgagttacagcaagaccctg | 44 | 84 |
| 107837 | 3' UTR | 3 | 2473 | gaatatggcttcccatacc | 0 | 85 |
| 107838 | 3' UTR | 3 | 2502 | ccctaaatcatgtccagagc | 87 | 86 |
| 107839 | 3' UTR | 3 | 2558 | gacttggaatggcggaggct | 74 | 87 |
| 107840 | 3' UTR | 3 | 2587 | caaatcacggtctgctcaag | 31 | 88 |
| 107841 | 3' UTR | 3 | 2618 | gaagtgtggttttccagcagg | 56 | 89 |
| 107842 | 3' UTR | 3 | 2648 | cctaaaggaccgtcacccag | 42 | 90 |
| 107843 | 3' UTR | 3 | 2678 | gtgaaccgggacagagacgg | 25 | 91 |
| 107844 | 3' UTR | 3 | 2724 | gccccacaggggtttgaggt | 53 | 92 |
| 107845 | 3' UTR | 3 | 2755 | cctttgcaggaagagtcgtg | 75 | 93 |
| 107846 | 3' UTR | 3 | 2785 | aaagccacttaatgtggagg | 79 | 94 |
| 107847 | 3' UTR | 3 | 2844 | gtgaaaatgctggcaagaga | 86 | 95 |
| 107848 | 3' UTR | 3 | 2970 | tcagaatgcttacagcctgg | 61 | 96 |

As shown in Table 1, SEQ ID NOs 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, and 96 demonstrated at least 35% inhibition of human PTP1B expression in this assay and are therefore preferred.

Example 16
Antisense Inhibition of Rat PTP1B Expression by Chimeric Phosphorothioate Oligonucleotides Having 2'-MOE Wings and a Deoxy Gap In accordance with the present invention, a second series of oligonucleotides were designed to target different regions of the rat PTP1B RNA, using published sequences (GenBank accession number M33962, incorporated herein as SEQ ID NO: 10). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on rat PTP1B mRNA levels by quantitative real-time PCR as described in other examples herein. Data are averages from two experiments. If present, "N.D." indicates "no data".

TABLE 2

Inhibition of rat PTP1B mRNA levels by chimeric phosphorothioate oligonucleotides having 2'-MOE wings and a deoxy gap

| ISIS # | RE-GION | TARGET SEQ ID NO | TARGET SITE | SEQUENCE | % INHIB | SEQ ID NO |
|---|---|---|---|---|---|---|
| 111549 | 5' UTR | 10 | 1 | caacctccccagcagcggct | 32 | 97 |
| 111550 | 5' UTR | 10 | 33 | tcgaggcccgtcgcccgcca | 27 | 98 |
| 111551 | 5' UTR | 10 | 73 | cctcggccgtccgccgcgct | 34 | 99 |
| 111552 | Coding | 10 | 132 | tcgatctgctcgaattcctt | 49 | 100 |
| 113669 | Coding | 10 | 164 | cctggtaaatagccgcccag | 36 | 101 |
| 113670 | Coding | 10 | 174 | tgtcgaatatcctggtaaat | 63 | 102 |
| 113671 | Coding | 10 | 184 | actggcttcatgtcgaatat | 58 | 103 |
| 113672 | Coding | 10 | 189 | aagtcactggcttcatgtcg | 40 | 104 |
| 111553 | Coding | 10 | 190 | gaagtcactggcttcatgtc | 27 | 105 |
| 113673 | Coding | 10 | 191 | ggaagtcactggcttcatgt | 54 | 106 |
| 113674 | Coding | 10 | 192 | gggaagtcactggcttcatg | 41 | 107 |
| 113675 | Coding | 10 | 193 | tgggaagtcactggcttcat | 56 | 108 |
| 113676 | Coding | 10 | 194 | atgggaagtcactggcttca | 31 | 109 |
| 113677 | Coding | 10 | 195 | catgggaagtcactggcttc | 59 | 110 |
| 113678 | Coding | 10 | 225 | tttttgttcttaggaagttt | 24 | 111 |
| 111554 | Coding | 10 | 228 | cggtttttgttcttaggaag | 45 | 112 |
| 111555 | Coding | 10 | 269 | tccgactgtggtcaaaaggg | 39 | 113 |
| 113679 | Coding | 10 | 273 | ttaatccgactgtggtcaaa | 45 | 114 |
| 113680 | Coding | 10 | 298 | atagtcattatcttcctgat | 49 | 115 |
| 111556 | Coding | 10 | 303 | ttgatatagtcattatcttc | 29 | 116 |
| 113681 | Coding | 10 | 330 | gcttcctccatttttatcaa | 67 | 117 |
| 111557 | Coding | 10 | 359 | ggccctgggtgaggatatag | 20 | 118 |
| 113682 | Coding | 10 | 399 | cacaccatctcccagaagtg | 29 | 119 |
| 111558 | Coding | 10 | 405 | tgctcccacaccatctccca | 48 | 120 |
| 113683 | Coding | 10 | 406 | ctgctcccacaccatctccc | 51 | 121 |
| 113684 | Coding | 10 | 407 | tctgctcccacaccatctcc | 37 | 122 |
| 113685 | Coding | 10 | 408 | ttctgctcccacaccatctc | 54 | 123 |
| 113686 | Coding | 10 | 417 | cccctgctcttctgctccca | 60 | 124 |
| 111559 | Coding | 10 | 438 | atgcggttgagcatgaccac | 15 | 125 |
| 113687 | Coding | 10 | 459 | tttaacgagcctttctccat | 33 | 126 |
| 113688 | Coding | 10 | 492 | ttttcttctttctgtggcca | 54 | 127 |
| 113689 | Coding | 10 | 502 | gaccatctcttttcttcttct | 58 | 128 |
| 111560 | Coding | 10 | 540 | tcagagatcagtgtcagctt | 21 | 129 |
| 113690 | Coding | 10 | 550 | cttgacatcttcagagatca | 64 | 130 |
| 113691 | Coding | 10 | 558 | taatatgacttgacatcttc | 46 | 131 |
| 111561 | Coding | 10 | 579 | aactccaactgccgtactgt | 14 | 132 |
| 111562 | Coding | 10 | 611 | tctctcgagcctcctgggta | 38 | 133 |
| 113692 | Coding | 10 | 648 | ccaaagtcaggccaggtggt | 63 | 134 |
| 111563 | Coding | 10 | 654 | gggactccaaagtcaggcca | 31 | 135 |
| 113693 | Coding | 10 | 655 | agggactccaaagtcaggcc | 50 | 136 |
| 113694 | Coding | 10 | 656 | cagggactccaaagtcaggc | 45 | 137 |
| 113695 | Coding | 10 | 657 | tcagggactccaaagtcagg | 49 | 138 |
| 113696 | Coding | 10 | 663 | ggtgactcagggactccaaa | 34 | 139 |
| 111564 | Coding | 10 | 705 | cctgactctcggactttgaa | 53 | 140 |
| 113697 | Coding | 10 | 715 | gctgagtgagcctgactctc | 57 | 141 |
| 113698 | Coding | 10 | 726 | ccgtgctctgggctgagtga | 48 | 142 |
| 111565 | Coding | 10 | 774 | aaggtccctgacctgccaat | 28 | 143 |
| 111566 | Coding | 10 | 819 | tcttttcctcttgtccatcag | 34 | 144 |
| 113699 | Coding | 10 | 820 | gtcttttcctcttgtccatca | 41 | 145 |
| 113700 | Coding | 10 | 821 | ggtcttttcctcttgtccatc | 66 | 146 |
| 113701 | Coding | 10 | 822 | gggtcttttcctcttgtccat | 71 | 147 |
| 113702 | Coding | 10 | 852 | aacagcacttttcttgatgtc | 39 | 148 |
| 111567 | Coding | 10 | 869 | ggaacctgcgcatctccaac | 0 | 149 |
| 111568 | Coding | 10 | 897 | tggtcggccgtctggatgag | 29 | 150 |
| 113703 | Coding | 10 | 909 | gagaagcgcagttggtcggc | 48 | 151 |

TABLE 2-continued

Inhibition of rat PTP1B mRNA levels by chimeric phosphorothioate oligonucleotides having 2'-MOE wings and a deoxy gap

| ISIS # | RE-GION | TARGET SEQ ID NO | TAR-GET SITE | SEQUENCE | % INHIB | SEQ ID NO |
|---|---|---|---|---|---|---|
| 113704 | Coding | 10 | 915 | aggtaggagaagcgcagttg | 31 | 152 |
| 113705 | Coding | 10 | 918 | gccaggtaggagaagcgcag | 41 | 153 |
| 111569 | Coding | 10 | 919 | agccaggtaggagaagcgca | 56 | 154 |
| 113706 | Coding | 10 | 920 | cagccaggtaggagaagcgc | 58 | 155 |
| 113707 | Coding | 10 | 921 | acagccaggtaggagaagcg | 43 | 156 |
| 113708 | Coding | 10 | 922 | cacagccaggtaggagaagc | 49 | 157 |
| 113709 | Coding | 10 | 923 | tcacagccaggtaggagaag | 47 | 158 |
| 111570 | Coding | 10 | 924 | atcacagccaggtaggagaa | 51 | 159 |
| 113710 | Coding | 10 | 925 | gatcacagccaggtaggaga | 51 | 160 |
| 113711 | Coding | 10 | 926 | cgatcacagccaggtaggag | 63 | 161 |
| 113712 | Coding | 10 | 927 | tcgatcacagccaggtagga | 71 | 162 |
| 113713 | Coding | 10 | 932 | caccctcgatcacagccagg | 75 | 163 |
| 113714 | Coding | 10 | 978 | tccttccactgatcctgcac | 97 | 164 |
| 111571 | Coding | 10 | 979 | ctccttccactgatcctgca | 89 | 165 |
| 113715 | Coding | 10 | 980 | gctccttccactgatcctgc | 99 | 166 |
| 107799 | Coding | 10 | 981 | agctccttccactgatcctg | 99 | 167 |
| 113716 | Coding | 10 | 982 | aagctccttccactgatcct | 97 | 168 |
| 113717 | Coding | 10 | 983 | aaagctccttccactgatcc | 95 | 169 |
| 113718 | Coding | 10 | 984 | gaaagctccttccactgatc | 95 | 170 |
| 113719 | Coding | 10 | 985 | ggaaagctccttccactgat | 95 | 171 |
| 111572 | Coding | 10 | 986 | gggaaagctccttccactga | 89 | 172 |
| 113720 | Coding | 10 | 987 | tgggaaagctccttccactg | 97 | 173 |
| 113721 | Coding | 10 | 1036 | tggccggggaggtggggca | 20 | 174 |
| 111573 | Coding | 10 | 1040 | tgggtggccggggaggtggg | 20 | 175 |
| 113722 | Coding | 10 | 1046 | tgcgtttgggtggccgggga | 18 | 176 |
| 111574 | Coding | 10 | 1073 | tgcacttgccattgtgaggc | 38 | 177 |
| 113723 | Coding | 10 | 1206 | acttcagtgtcttgactcat | 67 | 178 |
| 113724 | Coding | 10 | 1207 | aacttcagtgtcttgactca | 60 | 179 |
| 111575 | Coding | 10 | 1208 | taacttcagtgtcttgactc | 50 | 180 |
| 113725 | Coding | 10 | 1209 | ctaacttcagtgtcttgact | 53 | 181 |
| 111576 | Coding | 10 | 1255 | gacagatgcctgagcactt | 32 | 182 |
| 106409 | Coding | 10 | 1333 | gaccaggaagggcttccagt | 32 | 183 |
| 113726 | Coding | 10 | 1334 | tgaccaggaagggcttccag | 39 | 184 |
| 111577 | Coding | 10 | 1335 | ttgaccaggaagggcttcca | 32 | 185 |
| 113727 | Coding | 10 | 1336 | gttgaccaggaagggcttcc | 41 | 186 |
| 113728 | Coding | 10 | 1342 | gcacacgttgaccaggaagg | 59 | 187 |
| 111578 | Coding | 10 | 1375 | gaggtacgcgccagtcgcca | 45 | 188 |
| 111579 | Coding | 10 | 1387 | tacccggtaacagaggtacg | 32 | 189 |
| 111580 | Coding | 10 | 1397 | agtgaaaacatacccggtaa | 30 | 190 |
| 111581 | 3' UTR | 10 | 1456 | caaatcctaacctgggcagt | 31 | 191 |
| 111582 | 3' UTR | 10 | 1519 | ttccagttccaccacaggct | 24 | 192 |
| 111583 | 3' UTR | 10 | 1552 | ccagtgcacagatgccctc | 47 | 193 |
| 111584 | 3' UTR | 10 | 1609 | acaggttaaggccctgagat | 29 | 194 |
| 111585 | 3' UTR | 10 | 1783 | gcctagcatcttttgttttc | 43 | 195 |
| 111586 | 3' UTR | 10 | 1890 | aagccagcaggaactttaca | 36 | 196 |
| 111587 | 3' UTR | 10 | 2002 | gggacacctgagggaagcag | 16 | 197 |
| 111588 | 3' UTR | 10 | 2048 | ggtcatctgcaagatggcgg | 40 | 198 |
| 111589 | 3' UTR | 10 | 2118 | gccaacctctgatgaccctg | 25 | 199 |
| 111590 | 3' UTR | 10 | 2143 | tggaagcccagctctaagc | 25 | 200 |
| 111591 | 3' UTR | 10 | 2165 | tagtaatgactttccaatca | 44 | 201 |
| 111592 | 3' UTR | 10 | 2208 | tgagtcttgcttacacctc | 41 | 202 |
| 111593 | 3' UTR | 10 | 2252 | cctgcgcgcggagtgacttc | 22 | 203 |
| 111594 | 3' UTR | 10 | 2299 | aggacgtcactgcagcagga | 43 | 204 |
| 111595 | 3' UTR | 10 | 2346 | tcaggacaagtcttggcagt | 32 | 205 |
| 111596 | 3' UTR | 10 | 2405 | gaggctgcacagtaagcgct | 34 | 206 |
| 111597 | 3' UTR | 10 | 2422 | tcagccaaccagcatcagag | 20 | 207 |
| 111598 | 3' UTR | 10 | 2449 | acccacagtgtccacctccc | 30 | 208 |
| 111599 | 3' UTR | 10 | 2502 | agtgcgggctgtgctgctgg | 30 | 209 |
| 111600 | 3' UTR | 10 | 2553 | cagctcgctctggcggcctc | 8 | 210 |
| 111601 | 3' UTR | 10 | 2608 | aggaagggagctgcacgtcc | 32 | 211 |
| 111602 | 3' UTR | 10 | 2664 | ccctcacgattgctcgtggg | 24 | 212 |
| 111603 | 3' UTR | 10 | 2756 | cagtggagcggctcctctgg | 18 | 213 |
| 111604 | 3' UTR | 10 | 2830 | caggctgacacacttacacgg | 30 | 214 |
| 111605 | 3' UTR | 10 | 2883 | gtcctacctcaaccctaaga | 37 | 215 |
| 111606 | 3' UTR | 10 | 2917 | ctgccccagcaccagccaca | 12 | 216 |
| 111607 | 3' UTR | 10 | 2946 | attgcttctaagaccctcag | 33 | 217 |
| 111608 | 3' UTR | 10 | 2978 | ttacatgtcaccactgttgt | 28 | 218 |
| 111609 | 3' UTR | 10 | 3007 | tacacatgtcatcagtagcc | 37 | 219 |
| 111610 | 3' UTR | 10 | 3080 | ttttctaactcacagggaaa | 30 | 220 |
| 111611 | 3' UTR | 10 | 3153 | gtgcccgccagtgagcaggc | 23 | 221 |
| 111612 | 3' UTR | 10 | 3206 | cggcctcggcactggacagc | 27 | 222 |
| 111613 | 3' UTR | 10 | 3277 | gtggaatgtctgagatccag | 31 | 223 |
| 111614 | 3' UTR | 10 | 3322 | agggcgggcctgcttgccca | 23 | 224 |
| 111615 | 3' UTR | 10 | 3384 | cggtcctggcctgctccaga | 31 | 225 |
| 111616 | 3' UTR | 10 | 3428 | tacactgttcccaggagggt | 42 | 226 |
| 111617 | 3' UTR | 10 | 3471 | tggtgccagcagcgctagca | 10 | 227 |
| 111618 | 3' UTR | 10 | 3516 | cagtctcttcagcctcaaga | 43 | 228 |
| 113729 | 3' UTR | 10 | 3537 | aagagtcatgagcaccatca | 56 | 229 |
| 111619 | 3' UTR | 10 | 3560 | tgaaggtcaagttcccctca | 40 | 230 |
| 111620 | 3' UTR | 10 | 3622 | ctggcaagaggcagactgga | 30 | 231 |
| 111621 | 3' UTR | 10 | 3666 | ggctctgtgctggcttctct | 52 | 232 |
| 111622 | 3' UTR | 10 | 3711 | gccatctcctcagcctgtgc | 39 | 233 |
| 111623 | 3' UTR | 10 | 3787 | agcgcctgctctgaggcccc | 16 | 234 |
| 111624 | 3' UTR | 10 | 3854 | tgctgagtaagtattgactt | 35 | 235 |
| 111625 | 3' UTR | 10 | 3927 | ctatggccatttagagagag | 36 | 236 |
| 113730 | 3' UTR | 10 | 3936 | tggtttattctatggccatt | 59 | 237 |
| 111626 | 3' UTR | 10 | 3994 | cgctcctgcaaaggtgctat | 11 | 238 |
| 111627 | 3' UTR | 10 | 4053 | gttggaaacggtgcagtcgg | 39 | 239 |
| 111628 | 3' UTR | 10 | 4095 | atttattgttgcaactaatg | 33 | 240 |

As shown in Table 2, SEQ ID NOs 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 167, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 and 240 demonstrated at least 30% inhibition of rat PTP1B expression in this experiment and are therefore preferred.

Example 17
Western Blot Analysis of PTP1B Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to PTP1B is used, with a radiolabelled or fluorescently labeled secondary antibody directed against the primary antibody species. Bands are visualized using a PHOSPHORIMAGER™ (Molecular Dynamics, Sunnyvale Calif.).

Example 18
Effects of Antisense Inhibition of PTP1B (ISIS 113715) on Blood Glucose Levels db/db mice are used as a model of Type 2 diabetes. These mice are hyperglycemic, obese, hyperlipidemic, and insulin resistant. The db/db phenotype is due to a mutation in the leptin receptor on a C57BLKS background. However, a mutation in the leptin gene on a different mouse background can produce obesity without diabetes (ob/ob mice). Leptin is a hormone produced by fat that regulates appetite and animals or humans with leptin deficiencies become obese. Heterozygous db/wt mice (known as lean littermates) do not display the hyperglycemia/hyperlipidemia or obesity phenotype and are used as controls.

In accordance with the present invention, ISIS 113715 (GCTCCTTCCACTGATCCTGC, SEQ ID No: 166) was investigated in experiments designed to address the role of PTP1B in glucose metabolism and homeostasis. ISIS 113715 is completely complementary to sequences in the coding region of the human, rat, and mouse PTP1B nucleotide sequences incorporated herein as SEQ ID No: 3 (starting at nucleotide 951 of human PTP1B; Genbank Accession No. M31724), SEQ ID No: 10 (starting at nucleotide 980 of rat PTP1B; Genbank Accession No. M33962) and SEQ ID No: 241 (starting at nucleotide 1570 of mouse PTP1B; Genbank Accession No. U24700). The control used is ISIS 29848 (NNNNNNNNNNNNNNNNNNNN, SEQ ID No: 242) where N is a mixture of A, G, T and C.

Male db/db mice and lean (heterozygous, i.e., db/wt) littermates (age 9 weeks at time 0) were divided into matched groups (n=6) with the same average blood glucose levels and treated by intraperitoneal injection once a week with saline, ISIS 29848 (the control oligonucleotide) or ISIS 113715. db/db mice were treated at a dose of 10, 25 or 50 mg/kg of ISIS 113715 or 50 mg/kg of ISIS 29848 while lean littermates were treated at a dose of 50 or 100 mg/kg of ISIS 113715 or 100 mg/kg of ISIS 29848. Treatment was continued for 4 weeks with blood glucose levels being measured on day 0, 7, 14, 21 and 28.

By day 28 in db/db mice, blood glucose levels were reduced at all doses from a starting level of 300 mg/dL to 225 mg/dL for the 10 mg/kg dose, 175 mg/dL for the 25 mg/kg dose and 125 mg/dL for the 50 mg/kg dose. These final levels are within normal range for wild-type mice (170 mg/dL). The mismatch control and saline treated levels levels were 320 mg/dL and 370 mg/dL at day 28, respectively.

In lean littermates, blood glucose levels remained constant throughout the study for all treatment groups (average 120 mg/dL). These results indicate that treatment with ISIS 113715 reduces blood glucose in db/db mice and that there is no hypoglycemia induced in the db/db or the lean littermate mice as a result of the oligonucleotide treatment.

In a similar experiment, ob/ob mice and their lean littermates (heterozygous, i.e., ob/wt) were dosed twice a week at 50 mg/kg with ISIS 113715, ISIS 29848 or saline control and blood glucose levels were measured at the end of day 7, 14 and 21. Treatment of ob/ob mice with ISIS 113715 resulted in the largest decrease in blood glucose over time going from 225 mg/dL at day 7 to 95 mg/dL at day 21. Ob/ob mice displayed an increase in plasma glucose over time from 300 mg/dL to 325 mg/dL while treatment with the control oligonucleotide reduced plasma glucose from an average of 280 mg/dL to 130 mg/dL. In the lean littermates plasma glucose levels remained unchanged in all treatment groups (average level 100 mg/dL).

Example 19
Effects of Antisense Inhibition of PTP1B (ISIS 113715) on mRNA Expression in Liver Male db/db mice and lean littermates (age 9 weeks at time 0) were divided into matched groups (n=6) with the same average blood glucose levels and treated by intraperitoneal injection once a week with saline, ISIS 29848 (the control oligonucleotide) or ISIS 113715. db/db mice were treated at a dose of 10, 25 or 50 mg/kg of ISIS 113715 or 50 mg/kg of ISIS 29848 while lean littermates were treated at a dose of 50 or 100 mg/kg of ISIS 113715 or 100 mg/kg of ISIS 29848. Treatment was continued for 4 weeks after which the mice were sacrificed and tissues collected for mRNA analysis. RNA values were normalized and are expressed as a percentage of saline treated control.

ISIS 113715 successfully reduced PTP1B mRNA levels in the livers of db/db mice at all doses examined (60% reduction of PTP1B mRNA), whereas the control oligonucleotide treated animals showed no reduction in PTP1B mRNA, remaining at the level of the saline treated control. Treatment of lean littermates with ISIS 113715 also reduced mRNA levels to 45% of control at the 50 mg/kg dose and 25% of control at the 100 mg/kg dose. The control oligonucleotide (ISIS 29848) failed to show any reduction in mRNA levels.

Example 20
Effects of Antisense Inhibition of PTP1B (ISIS 113715) on Body Weight Male db/db mice and lean littermates (age 9 weeks at time 0) were divided into matched groups (n=6) with the same average blood glucose levels and treated by intraperitoneal injection once a week with saline, ISIS 29848 (the control oligonucleotide) or ISIS 113715. db/db mice were treated at a dose of 10, 25 or 50 mg/kg of ISIS 113715 or 50 mg/kg of ISIS 29848 while lean littermates were treated at a dose of 50 or 100 mg/kg of ISIS 113715 or 100 mg/kg of ISIS 29848. Treatment was continued for 4 weeks. At day 28 mice were sacrificed and final body weights were measured.

Treatment of ob/ob mice with ISIS 113715 resulted in an increase in body weight which was constant over the dose range with animals gaining an average of 11.0 grams while saline treated controls gained 5.5 grams. Animals treated with the control oligonucleotide gained an average of 7.8 grams of body weight.

Lean littermate animals treated with 50 or 100 mg/kg of ISIS 113715 gained 3.8 grams of body weight compared to a gain of 3.0 grams for the saline controls.

In a similar experiment, ob/ob mice and their lean littermates were dosed twice a week at 50 mg/kg with ISIS 113715, ISIS 29848 or saline control and body weights were measured at the end of day 7, 14 and 21.

Treatment of the ob/ob mice with ISIS 113715, ISIS 29848 or saline control all resulted in a similar increase in body weight across the 21-day timecourse. At the end of day 7 all ob/ob treatment groups had an average weight of 42 grams. By day 21, animals treated with ISIS 113715 had an average body weight of 48 grams, while those in the ISIS 29848 (control oligonucleotide) and saline control group each had an average body weight of 52 grams. All of the lean littermates had an average body weight of 25 grams at the beginning of the timecourse and all lean littermate treatment groups showed an increase in body weight, to 28 grams, by day 21.

Example 21
Effects of Antisense Inhibition of PTP1B (ISIS 113715) on Plasma Insulin Levels Male db/db mice (age 9 weeks at time 0) were divided into matched groups (n=6) with the same average blood glucose levels and treated by intraperitoneal injection twice a week with saline, ISIS 29848 (the control oligonucleotide) or ISIS 113715 at a dose of 50 mg/kg. Treatment was continued for 3 weeks with plasma insulin levels being measured on day 7, 14, and 21.

Mice treated with ISIS 113715 showed a decrease in plasma insulin levels from 15 ng/mL at day 7 to 7.5 ng/mL on day 21. Saline treated animals has plasma insulin levels of 37 ng/mL at day 7 which dropped to 25 ng/mL on day 14 but rose again to 33 ng/mL by day 21. Mice treated with the control oligonucleotide also showed a decrease in plasma insulin levels across the timecourse of the study from 25 ng/mL at day 7 to 10 ng/mL on day 21. However, ISIS 113715 was the most effective at reducing plasma insulin over time.

What is claimed is:

1. A method of decreasing blood glucose levels in an animal comprising administering to said animal an effective amount of a compound 8 to 50 nucleobases in length targeted to a nucleic acid molecule encoding PTP1B, wherein said compound specifically hybridizes with and inhibits the expression of PTP1B.

2. The method according to claim 1, wherein said compound is an antisense oligonucleotide.

3. The method according to claim 2, wherein said antisense oligonucleotide has a sequence comprising SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 or 240.

4. The method according to claim 2, wherein said antisense oligonucleotide is a sequence of up to 30 nucleobases in length comprising at least an 8 nucleobase portion of SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 or 240.

5. The method according to claim 2, wherein said antisense oligonucleotide has a sequence consisting of SEQ ID NO: 166.

6. The method according to claim 2, wherein said antisense oligonucleotide has a sequence consisting of SEQ ID NO: 20.

7. The method according to claim 2, wherein the antisense oligonucleotide comprises at least one modified internucleoside linkage.

8. The method according to claim 7, wherein the modified internucleoside linkage is a phosphorothioate linkage.

9. The method according to claim 2, wherein the antisense oligonucleotide comprises at least one modified sugar moiety.

10. The method according to claim 9, wherein the modified sugar moiety is a 2'-O-methoxyethyl sugar moiety.

11. The method according to claim 2, wherein the antisense oligonucleotide comprises at least one modified nucleobase.

12. The method according to claim 11, wherein the modified nucleobase is a 5-methylcytosine.

13. The method according to claim 2, wherein the antisense oligonucleotide is a chimeric oligonucleotide.

14. The method according to claim 1, when said compound is administered as a composition comprising said compound and a pharmaceutically acceptable carrier or diluent.

15. The method according to claim 14, wherein said composition further comprises a colloidal dispersion system.

16. The method according to claim 1, wherein the animal is a diabetic animal.

17. The method according to claim 16, wherein the diabetic animal has Type 2 diabetes.

18. The method according to claim 1, wherein the animal is a human or a rodent.

19. The method according to claim 1, wherein the blood glucose levels are plasma glucose levels or serum glucose levels.

20. A method of preventing or delaying the onset of an increase in blood glucose or plasma insulin levels in an animal comprising administering to said animal an effective amount of a compound 8 to 50 nucleobases in length targeted to a nucleic acid molecule encoding PTP1B, wherein said compound specifically hybridizes with and inhibits the expression of PTP1B.

21. The method according to claim 20, wherein said antisense oligonucleotide has a sequence comprising SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235; 236, 237, 239 or 240.

22. The method according to claim 20, wherein said antisense oligonucleotide is a sequence of up to 30 nuceobases in length comprising at least an 8 nucleobase portion of SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 or 240.

23. The method according to claim 20, wherein said compound is administered as a composition comprising said compound and a pharmaceutically acceptable carrier or diluent.

24. The method according to claim 23, wherein said composition further comprises a colloidal dispersion system.

25. The method according to claim 20, wherein the animal is a diabetic animal.

26. The method according to claim 25, wherein the diabetic animal has Type 2 diabetes.

27. The method according to claim 20, wherein the animal is a human or a rodent.

28. The method according to claim 20, wherein the blood glucose levels are plasma glucose levels or serum glucose levels.

29. The method according to claim 20, wherein said compound is an antisense oligonucleotide.

30. The method according to claim 29, wherein said antisense oligonucleotide has a sequence consisting of SEQ ID NO: 166.

31. The method according to claim 29, wherein said antisense oligonucleotide has a sequence consisting of SEQ ID NO: 20.

32. The method according to claim 29 wherein the antisense oligonucleotide comprises at least one modified internucleoside linkage.

33. The method according to claim 32, wherein the modified internucleoside linkage is a phosphorothioate linkage.

34. The method according to claim 29, wherein the antisense oligonucleotide comprises at least one modified sugar moiety.

35. The method according to claim 34, wherein the modified sugar moiety is a 2'-O-methoxyethyl sugar moiety.

36. The method according to claim 29, wherein the antisense oligonucleotide comprises at least one modified nucleobase.

37. The method according to claim 36, wherein the modified nucleobase is a 5-methylcytosine.

38. The method according to claim 29, wherein the antisense oligonucleotide is a chimeric oligonucleotide.

39. A method of decreasing plasma insulin levels in an animal comprising administering to said animal an effective amount of a compound 8 to 50 nucleobases in length targeted to a nucleic acid molecule encoding PTP1B, wherein said compound specifically hybridizes with and inhibits the expression of PTP1B.

40. The method according to claim 39, wherein said compound is an antisense oligonucleotide.

41. The method according to claim 40, wherein said antisense oligonucleotide has a sequence comprising SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 or 240.

42. The method according to claim 40, wherein said antisense oligonucleotide is a sequence of up to 30 nucleobases in length comprising at least an 8 nucleobase portion of SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 or 240.

43. The method according to claim 40, wherein said antisense oligonucleotide has a sequence consisting of SEQ ID NO: 166.

44. The method according to claim 40, wherein said antisense oligonucleotide has a sequence consisting of SEQ ID NO: 20.

45. The method according to claim 40, wherein the antisense oligonucleotide comprises at least one modified internucleoside linkage.

46. The method according to claim 45, wherein the modified internucleoside linkage is a phosphorotioate linkage.

47. The method according to claim 40, wherein the antisense oligonucleotide comprises at least one modified sugar moiety.

48. The method according to claim 47, wherein the modified sugar moiety is a 2'-O-methoxyethyl sugar moiety.

49. The method according to claim 40, wherein the antisense oligonucleotide comprises at least one modified nucleobase.

50. The method according to claim 49, wherein the modified nucleobase is a 5-methylcytosine.

51. The method according to claim 40, wherein the antisense oligonucleotide is a chimeric oligonucleotide.

52. The method according to claim 39, wherein said compound is administered as a composition comprising said compound and a pharmaceutically acceptable carrier or diluent.

53. The method according to claim 52, wherein said composition further comprises a colloidal dispersion system.

54. The method according to claim 39, wherein the animal is a diabetic animal.

55. The method according to claim 54, wherein the diabetic animal has Type 2 diabetes.

56. The method according to claim 39, wherein the animal is a human or a rodent.

57. A method of treating or delaying the onset of Type 2 diabetes in an animal comprising administering to said animal an effective amount of a compound 8 to 50 nucleobases in length targeted to a nucleic acid molecule encoding PTP1B, wherein said compound specifically hybridizes with and inhibits the expression of PTP1B.

58. The method according to claim 57, wherein said compound is administered as a composition comprising said compound and a pharmaceutically acceptable carrier or diluent.

59. The method according to claim 58, wherein said composition further comprises a colloidal dispersion system.

60. The method according to claim 57, wherein the animal is a human or a rodent.

61. The method according to claim 57, wherein said compound is an antisense oligonucleotide.

62. The method according to claim 61, wherein said antisense oligonucleotide has a sequence comprising SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 or 240.

63. The method according to claim 61, wherein said antisense oligonucleotide is a sequence of up to 30 nuceobases in length comprising at least an 8 nucleobase portion of SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 or 240.

64. The method according to claim 61, wherein said antisense oligonucleotide has a sequence consisting of SEQ ID NO: 166.

65. The method according to claim 61, wherein said antisense oligonucleotide has a sequence consisting of SEQ ID NO: 20.

66. The method according to claim 61, wherein the antisense oligonucleotide comprises at least one modified internucleoside linkage.

67. The method according to claim 66, wherein the modified internucleoside linkage is a phosphorothioate linkage.

68. The method according to claim 66, wherein the antisense oligonucleotide comprises at least one modified sugar moiety.

69. The method according to claim 68, wherein the modified sugar moiety is a 2'-O-methoxyethyl sugar moiety.

70. The method according to claim 66, wherein the antisense oligonucleotide comprises at least one modified nucleobase.

71. The method according to claim 70, wherein the modified nucleobase is a 5-methylcytosine.

72. The method according to claim 66, wherein the antisense oligonucleotide is a chimeric oligonucleotide.

* * * * *

UNITED STATES PATENT AND TRADEMARK OFFICE
CERTIFICATE OF CORRECTION

PATENT NO. : 6,602,857 B1
DATED : August 5, 2003
INVENTOR(S) : Lex M. Cowsert et al.

It is certified that error appears in the above-identified patent and that said Letters Patent is hereby corrected as shown below:

<u>Column 2,</u>
Line 15, delete "i".

<u>Column 10,</u>
Line 5, delete "5,580,731"

<u>Column 27,</u>
Line 16, replace "5 2,2-Anhydro" with -- 2,2-Anhydro --.
Line 59, replace "-5'-dimethoxytrityl" with -- -5'-O- dimethoxytrityl --.

<u>Column 28,</u>
Line 33, replace "3'-acetyl-2'- Methoxyethyl" with
3'-O-acetyl-2'-O-methoxyethyl edges --.
Line 51, replace "85 g, 0.134 M)" with -- (85 g, 0.134 M) --

<u>Column 31,</u>
Line 25, replace "dimethylaminooxyethyl]-methyluridine" with
-- dimethylaminooxythyl]-5-methyluridine --.
Line 62, replace "for hrs" with -- for 4 hrs --

<u>Column 37,</u>
Line 60, replace "5770" with -- 15770 --.

<u>Column 40,</u>
Line 38, replace "DATP" with -- dATP --.

<u>Column 43,</u>
Line 13, Table 1, replace "1351 tagcagaggtaagcgccygc" with
-- 1351 tagcagaggtaagcgcggc --.

<u>Column 47,</u>
Lines 30 and 31, replace "treated levels levels were" with -- treated levels were --.

UNITED STATES PATENT AND TRADEMARK OFFICE
CERTIFICATE OF CORRECTION

PATENT NO. : 6,602,857 B1
DATED : August 5, 2003
INVENTOR(S) : Lex M. Cowsert et al.

It is certified that error appears in the above-identified patent and that said Letters Patent is hereby corrected as shown below:

<u>Column 48,</u>
Line 60, replace "has" with -- had --.

Signed and Sealed this

Twenty-third Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,602,857 B1　　　　　　　　　　　　　　　　　　　　　　　Page 1 of 1
DATED : August 5, 2003
INVENTOR(S) : Lex M. Cowsert et al.

It is certified that error appears in the above-identified patent and that said Letters Patent is hereby corrected as shown below:

<u>Title page,</u>
Item [73], Assignee, should read -- Isis Pharmaceuticals, Inc. --

Signed and Sealed this

Seventeenth Day of February, 2004

JON W. DUDAS
*Acting Director of the United States Patent and Trademark Office*